US011701354B2

(12) United States Patent
Taylor et al.

(10) Patent No.: US 11,701,354 B2
(45) Date of Patent: Jul. 18, 2023

(54) PYRAZOLO[3,4-B]PYRAZINE DERIVATIVES AS SHP2 PHOSPHATASE INHIBITORS

(71) Applicants: Relay Therapeutics, Inc., Cambridge, MA (US); D. E. Shaw Research, LLC, New York, NY (US)

(72) Inventors: Alexander M. Taylor, Cambridge, MA (US); W. Patrick Walters, Westborough, MA (US); Mark Andrew Murcko, Holliston, MA (US); Fabrizio Giordanetto, New York, NY (US); Eric Therrien, Bronx, NY (US); Sathesh Bhat, Jersey City, NJ (US); Markus Kristofer Dahlgren, Shelton, CT (US)

(73) Assignees: D. E. Shaw Research, LLC, New York, NY (US); Relay Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/651,733

(22) PCT Filed: Sep. 28, 2018

(86) PCT No.: PCT/US2018/053322
§ 371 (c)(1),
(2) Date: Mar. 27, 2020

(87) PCT Pub. No.: WO2019/067843
PCT Pub. Date: Apr. 4, 2019

(65) Prior Publication Data
US 2020/0253969 A1    Aug. 13, 2020

Related U.S. Application Data

(60) Provisional application No. 62/565,599, filed on Sep. 29, 2017.

(51) Int. Cl.
    A61K 31/4985    (2006.01)
    C07D 487/04     (2006.01)
    A61K 45/06      (2006.01)
    C07D 519/00     (2006.01)

(52) U.S. Cl.
    CPC .......... A61K 31/4985 (2013.01); A61K 45/06 (2013.01); C07D 487/04 (2013.01); C07D 519/00 (2013.01)

(58) Field of Classification Search
    CPC .......................... A61K 31/4985; C07D 487/04
    USPC .......................................... 514/249; 544/350
    See application file for complete search history.

(56) References Cited

U.S. PATENT DOCUMENTS

| 10,280,171 B2 | 5/2019 | Jones et al. |
| 2011/0130396 A1 | 6/2011 | Hoelzemann et al. |
| 2017/0001975 A1 | 1/2017 | Chen et al. |
| 2017/0015680 A1 | 1/2017 | Chen et al. |
| 2017/0204080 A1 | 7/2017 | Chen et al. |
| 2017/0342078 A1 | 11/2017 | Jones et al. |
| 2018/0186770 A1 | 7/2018 | Chen et al. |
| 2018/0251471 A1 | 9/2018 | Chen et al. |
| 2019/0077792 A1 | 3/2019 | Volkmann et al. |
| 2019/0127378 A1 | 5/2019 | Ma et al. |
| 2019/0185475 A1 | 6/2019 | Bagdanoff et al. |
| 2019/0210977 A1 | 7/2019 | Jogalekar et al. |
| 2019/0290649 A1 | 9/2019 | Xie et al. |
| 2019/0307745 A1 | 10/2019 | Albrecht et al. |
| 2019/0389867 A1 | 12/2019 | Jones et al. |
| 2020/0002330 A1 | 1/2020 | Chen et al. |
| 2020/0017511 A1 | 1/2020 | Blank et al. |
| 2020/0017517 A1 | 1/2020 | Gill et al. |
| 2020/0048249 A1 | 2/2020 | Jones et al. |
| 2020/0062760 A1 | 2/2020 | Giordanetto et al. |
| 2020/0108071 A1 | 4/2020 | Chin et al. |
| 2020/0115389 A1 | 4/2020 | Fu et al. |
| 2020/0172546 A1 | 6/2020 | Taylor et al. |

FOREIGN PATENT DOCUMENTS

| CN | 107286150 A | 10/2017 |
| CN | 110143949 A | 8/2019 |
| CN | 111153899 A | 5/2020 |
| TW | 201925186 A | 7/2019 |
| WO | WO-2004/111060 A1 | 12/2004 |
| WO | WO-2020076723 A1 | 1/2007 |
| WO | WO-2010/011666 A2 | 1/2010 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
U.S. Appl. No. 16/950,576, SHP2 Phosphatase Inhibitors and Methods of Use Thereof, filed Nov. 17, 2020.
Chloe, Copin et al. "Snar Versus Buchwald-Hartwig Amination/Amidation in the Imidazo[2,1-b] [1,3,4]thiadiazole Series," European Journal of Organic Chemistry, vol. 2015, No. 31, Sep. 29, 2015, pp. 6932-6942.
Larochelle, Jonathan et al. "Identification of an Allosteric Benzothiazolopyrimidone Inhibitor of the Oncogenic Protein Tyrosine Phosphatase SHP2," Bioorganic & Medicinal Chemistry, vol. 25, No. 24, Oct. 20, 2017, pp. 6479-6485.

(Continued)

Primary Examiner — Douglas M Willis
(74) Attorney, Agent, or Firm — Alston & Bird LLP

(57) ABSTRACT

Cellular biological activities are tightly controlled by intracellular signaling processes initiated by extracellular signals. Protein tyrosine phosphatases, which remove phosphate groups from tyrosine phosphorylated signaling molecules, play equally important tyrosine roles as protein kinases in signal transduction. SHP-2, a cytoplasmic SH2 domain containing protein tyrosine phosphatase, is involved in the signaling pathways of a variety of growth factors and cytokines. Recent studies have clearly demonstrated that this phosphatase plays an important role in transducing signal relay from the cell surface to the nucleus, and is a critical intracellular regulator in mediating cell proliferation and differentiation.

40 Claims, No Drawings

(56) References Cited

FOREIGN PATENT DOCUMENTS

| | | | |
|---|---|---|---|
| WO | WO-2010/097798 A1 | 9/2010 | |
| WO | WO-2010/121212 A2 | 10/2010 | |
| WO | WO-2011/130396 A1 | 10/2011 | |
| WO | WO 2015/107493 A1 | 7/2015 | |
| WO | WO-2015/107494 A1 | 7/2015 | |
| WO | WO-2015/107495 A1 | 7/2015 | |
| WO | WO-2016/203404 A1 | 12/2016 | |
| WO | WO-2016/203406 A1 | 12/2016 | |
| WO | WO-2017156397 A1 | 9/2017 | |
| WO | WO-2017/210134 A1 | 12/2017 | |
| WO | WO-2017/211303 A1 | 12/2017 | |
| WO | WO-2018/013597 A1 | 1/2018 | |
| WO | WO-2018/057884 A1 | 3/2018 | |
| WO | WO-2018/081091 A1 | 5/2018 | |
| WO | WO-2018/172984 A1 | 9/2018 | |
| WO | WO-2018/218133 A1 | 11/2018 | |
| WO | WO-2019051084 A1 | 3/2019 | |
| WO | WO-2019/067843 A1 | 4/2019 | |
| WO | WO-2019067843 A1 * | 4/2019 | .............. A61P 35/00 |
| WO | WO-2019/075265 A1 | 4/2019 | |
| WO | WO-2019118909 A1 | 6/2019 | |
| WO | WO-2019/165073 A1 | 8/2019 | |
| WO | WO-2019158019 A1 | 8/2019 | |
| WO | WO-2019/183364 A1 | 9/2019 | |
| WO | WO-2019/183367 A1 | 9/2019 | |
| WO | WO-2019167000 A1 | 9/2019 | |
| WO | WO-2019199792 A1 | 10/2019 | |
| WO | WO-2019233810 A1 | 12/2019 | |
| WO | WO-2020022323 A1 | 1/2020 | |
| WO | WO-2020063760 A1 | 4/2020 | |
| WO | WO-2020065452 A1 | 4/2020 | |
| WO | WO-2020065453 A1 | 4/2020 | |
| WO | WO-2020073945 A1 | 4/2020 | |
| WO | WO-2020073949 A1 | 4/2020 | |
| WO | WO-2020081848 A1 | 4/2020 | |
| WO | WO-2020094018 A1 | 5/2020 | |
| WO | WO-2020094104 A1 | 5/2020 | |

OTHER PUBLICATIONS

Temple, Kayla et al. "Identification of the Minimum PAR4 Inhibitor Pharmacophore and Optimization of a Series of 2-Methoxy-6-Arylimidazo[2,1-b][1,3,4]Thiadiazoles," Bioorganic & Medicinal Chemistry Letters, Pergamon, Amsterdam, NL, vol. 26, No. 22, 11 Oct. 11, 2016, pp. 5481-5486.

Yokoi, Taiyo et al. "Quantitative Structure-Activity Relationship of Substituted Imidazothiadiazoles for Their Binding Against the Ecdysone Receptor of Sf-9 Cells," Bioorganic & Medicinal Chemistry Letters, vol. 27, No. 23, Oct. 13, 2017, pp. 5305-5309.

Saifidin, Safarov et al. "Preparation of 5-Bromo-6-phenylimidazo(2,I-b)(I,3,4)thiadiazol-2-ylamines," Journal of Heterocyclic Chemistry, Wiley-Blackwell Publishing, Inc, Us, vol. 45, No. 1, Jan. 1, 2008, pp. 299-302.

Krasavin M et al. "Tert-Butyl Isocyanide Revisited as a Convertible Reagent in the Groebke-Blackburn Reaction," Tetrahedron Letters, Elsevier, Amsterdam, NL, vol. 49, No. 51, Dec. 15, 2008, pp. 7318-7321.

Shen, Jiayi et al. "3-Aminopyrazolopyrazine Derivatives as Spleen Tyrosine Kinase Inhibitors," Hemical Biology & Drug Design, vol. 88, No. 5, 2016, pp. 690-698.

Jorge, Fortanet et al. "Allosteric Inhibition of SHP2: Identification of a Potent, Selective, and Orally Efficacious Phosphatase Inhibitor," J. Med. Chem. 2016, 59, 17, pp. 7773-7782.

Bollu et al. Clin Cancer Res. May 1, 2017; 23(9): 2136-2142. (Year: 2017).

Lazo et al. SLAS Discovery 2017, vol. 22(9) 1071-1083 (Year: 2017).

Jones et al. U.S. Appl. No. 62/343,455, filed May 31, 2016. (Year: 2016).

International Search Report and Written Opinion for International Patent Application PCT/US2019/023389 dated May 10, 2019 (12 pages).

U.S. Appl. No. 16/616,361, filed Nov. 22, 2019.
U.S. Appl. No. 16/344,061, filed Mar. 22, 2019.
U.S. Appl. No. 16/971,435, filed Aug. 20, 2020.
U.S. Appl. No. 16/982,395, filed Sep. 18, 2020.
U.S. Appl. No. 16/982,401, filed Sep. 18, 2020.
U.S. Appl. No. 16/886,105, filed May 28, 2020.
U.S. Appl. No. 17/029,376, filed Sep. 23, 2020.

Hellmuth et al., Specific inhibitors of the protein tyrosine phosphatase Shp2 identified by high-throughput docking, PNAS, 105(20), 7275-7280, (2008).

Horig et al., "From bench to clinic and back: Perspective on the 1st IQPC Translational Research Conference" Journal of Translational Medicine, 2, 44, (Dec. 2004).

Schafer et al., "Failure is an option: learning from unsuccessful proof-of-concept trials," Drug Discovery Today, 13, 913-916, (Nov. 2018).

U.S. Appl. No. 16/335,933, Non-Final Office Action dated Jan. 8, 2020.

U.S. Appl. No. 16/355,061, Non-Final Office Action dated Feb. 19, 2021.

U.S. Appl. No. 16/355,061, Requirement for Restriction/Election dated Jul. 31, 2020.

U.S. Appl. No. 16/616,361, Non-Final Office Action dated May 13, 2021.

U.S. Appl. No. 16/616,361, Requirement for Restriction/Election dated Oct. 30, 2020.

U.S. Appl. No. 16/886,105, Notice of Allowance dated Sep. 9, 2020.
U.S. Appl. No. 16/886,105, Notice of Allowance dated Nov. 4, 2020.

U.S. Appl. No. 16/335,933, Final Office Action dated Aug. 26, 2020.
WIPO Application No. PCT/US2017/052950, PCT International Preliminary Report on Patentability dated Mar. 26, 2019.

WIPO Application No. PCT/US2017/052950, PCT International Search Report and Written Opinion of the International Searching Authority dated Mar. 29, 2018.

WIPO Application No. PCT/US2017/058048, PCT International Preliminary Report on Patentability dated Apr. 30, 2019.

WIPO Application No. PCT/US2017/058048, PCT International Search Report and Written Opinion of the International Searching Authority dated May 3, 2018.

WIPO Application No. PCT/US2018/034614, PCT International Preliminary Report on Patentability dated Nov. 26, 2019.

WIPO Application No. PCT/US2018/034614, PCT International Search Report and Written Opinion of the International Searching Authority dated Nov. 29, 2018.

WIPO Application No. PCT/US2018/053322, PCT International Preliminary Report on Patentability dated Mar. 31, 2020.

WIPO Application No. PCT/US2018/053322, PCT International Search Report and Written Opinion of the International Searching Authority dated Apr. 4, 2019.

WIPO Application No. PCT/US2019/023389, PCT International Preliminary Report on Patentability dated Sep. 22, 2020.

WIPO Application No. PCT/US2020/052118, PCT International Search Report and Written Opinion of the International Searching Authority dated Dec. 14, 2020.

Aceto, N., et al., "Tyrosine phosphate SHP2 promotes breast cancer progression and maintans tumor-initiating cells via activation of key transcription factors and a positive feedback signaling loop," Nature Medicine 18:529-537, (2012).

Chen, YN., et al. "Allosteric inhibition of SHP2 phosphate inhibits cancers driven by receptor tyrosine kinases," Nature, 535, 148-152, (2016).

* cited by examiner

PYRAZOLO[3,4-B]PYRAZINE DERIVATIVES AS SHP2 PHOSPHATASE INHIBITORS

CROSS REFERENCE TO RELATED APPLICATIONS

This application claims the benefit of, and priority to, U.S. provisional application Ser. No. 62/565,599 filed Sep. 29, 2017, the content of which is hereby incorporated by reference herein in its entirety.

BACKGROUND

Src homology region 2 (SH2)-containing protein tyrosine phosphatase 2 (SHP2) is a protein tyrosine phosphatase encoded by the PTPN11 gene. SHP2 contains two Src homology 2 (SH2) $NH_2$-terminal domains and a C-terminal protein-tyrosine phosphatase domain. It is ubiquitously expressed in various tissues and cell types. SHP2 plays an important role in diverse signaling pathways to regulate cellular biological processes and is involved in the signaling pathways of a variety of growth factors and cytokines. Within a single signaling pathway, SHP2 can play both positive (signal enhancing) and negative (signal diminishing) roles in intracellular signaling processes. SHP2 is believed to function by dephosphorylating its associated signaling molecules, thereby attenuating the local signaling flow. However, the main effect of SHP2 action in most signaling pathways (e.g., growth factor, cytokine, and extracellular matrix receptors) is to enhance signal transduction. For example, SHP2 is a positive regulator of the ERK/MAPK signaling pathway, playing a key role in regulating cellular proliferation and survival. (For a review of SHP2 phosphatase, see, e.g, K. S. Grossman et al., *Adv. Cancer Res.* 2010, 106, 53-89; and references cited therein.)

In the basal state, SHP2 is normally auto-inhibited due to intramolecular interactions between its N-terminal SH2 (N—SH2) domain and its catalytic (PTP) domain, which blocks access to the catalytic site. Activating proteins that interact with the SH2 domains induce a conformational change that reverses this inhibition and allows substrate access to the catalytic site. Mutations in the PTPN11 gene that affect the N—SH2 or PTP domain residues involved in basal inhibition of SHP2 result in more readily activatable forms of SHP2 protein, which can lead to unregulated or increased SHP2 activity. Such activated mutants of SHP2 have been associated with developmental disorders such as Noonan syndrome, where nearly all mutated forms of SHP2 demonstrate increased PTP activity. Thus, there is a need for SHP2 phosphatase inhibitor compounds and methods for treating cancer and other disorders with these compounds.

SUMMARY

It is understood that any of the embodiments described below can be combined in any desired way, and that any embodiment or combination of embodiments can be applied to each of the aspects described below, unless the context indicates otherwise.

In an embodiment, the present disclosure provides a compound of Formula I, or a pharmaceutically acceptable salt or stereoisomer thereof, wherein Formula I is represented by:

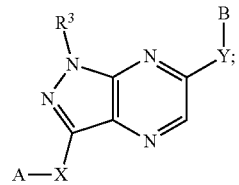

wherein
X is selected from the group consisting of a bond, —O—, —$NR^{X1}$—, —C(O)$NR^{X11}$—, —S(O)$_w$— (wherein w is 0, 1 or 2), —C(O)—, —C($R^{X2}R^{X3}$)—, —O—C($R^{X4}R^{X5}$)—, —C($R^{X4}R^{X5}$)—O—, —$NR^{X1}$—C($R^{X4}R^{X5}$)—, —C($R^{X4}R^{X5}$)—$NR^{X1}$—, —C=C($R^{X6}R^{X7}$)—, —C≡C—, and cyclopropyl;

Y is selected from the group consisting of —$NR^Y$—, —$C_{1-3}$alkylene-NR—, and —$NR^Y$—$C_{1-3}$alkylene-;

A is selected from the group consisting of a 6-10 membered monocyclic or bicyclic aryl, a 5-7 membered monocyclic heteroaryl having one or more heteroatoms each independently selected from O, S, or N, a 8-10 membered bicyclic heteroaryl having one or more heteroatoms each independently selected from O, S, or N; and a 4-7 membered heterocyclyl, wherein A may optionally be substituted by one, two, three or more substituents each independently selected from the group consisting of —$R^{10}$, —$OR^{10}$, —S(O)$_w R^{10}$ (wherein w is 0, 1 or 2), —N($R^{10}$)$_2$, —OS(O)$_w$—$R^{10}$ (wherein w is 0, 1, or 2), —S(O)$_w$—N($R^{10}$)$_2$ (wherein w is 0, 1 or 2), —N($R^{10}$)—S(O)$_w$—$R^{10}$ (wherein w is 0, 1 or 2), —S(O)$_w$—(NH)$R^{10}$, —N($R^{10}$)—S(O)—$R^{10}$, —P(O)($R^{10}$)$_2$, —C(O)$R^{10}$, —C(O)N($R^{10}$)$_2$, —$NR^{10}$—C(O)$R^{10}$, oxo, halogen and cyano;

$R^{10}$ is independently selected from the group consisting of hydrogen, $C_{1-6}$alkyl, $C_{3-6}$cycloalkyl, $C_{2-6}$heteroalkyl, heterocycloalkyl, aryl, and heteroaryl; wherein $C_{1-6}$alkyl, $C_{3-6}$cycloalkyl, $C_{2-6}$heteroalkyl, heterocycloalkyl, aryl, and heteroaryl may optionally be substituted by one, two, three or more substituents each independently selected from the group consisting of halogen, hydroxyl, —C(O)—$R^{20}$, —C($NR^a$)—$R^b$, —$NR^a R^b$, $C_{1-6}$alkyl, $C_{1-6}$haloalkyl and $C_{1-6}$alkoxy;

$R^2$ is selected from the group consisting of hydrogen, hydroxyl, halogen, —$NR^a R^b$, $C_{1-6}$alkyl and $C_{1-6}$alkoxy;

B is a 3-7 membered saturated carbocyclic or 4-7 membered saturated heterocyclic ring; wherein the heterocyclic ring B may have one or two heteroatoms each independently selected from the group consisting of O, S(O)$_w$ (wherein w is 0, 1, or 2), and $NR^h$;

carbocyclic or heterocyclic ring B may optionally be substituted on one or more available carbons by one, two, three or more substituents each independently selected from the group consisting of halogen, hydroxyl, cyano, oxo, —$NR^a R^b$, —$CO_2 H$, —C(O)—$NR^a R^b$, —S(O)$_2$—$NR^a R^b$, —$NR^a$—S(O)$_2$—$C_{1-6}$alkyl, $C_{1-6}$ alkyl, $C_{2-6}$alkenyl, $C_{2-4}$alkynyl, $C_{3-6}$cycloalkyl, $C_{1-6}$alkoxy, $C_{3-6}$alkenyloxy, $C_{3-4}$alkynyloxy, $C_{3-6}$cycloalkoxy, $C_{1-6}$alkylcarbonyl-, $C_{1-6}$alkoxycarbonyl, $C_{1-6}$alkyl-S(O)$_w$— (wherein w is 0, 1 or 2), $C_{1-6}$alkylcarbonyl-N($R^a$)—, $C_{1-6}$alkoxycarbonyl-N($R^a$)—, aryl and heteroaryl; wherein —$NR^a$—S(O)$_2$—$C_{1-6}$-alkyl, $C_{1-6}$alkyl, $C_{2-6}$alkenyl, $C_{2-4}$alkynyl, $C_{3-6}$cycloalkyl, $C_{1-6}$ alkoxy, $C_{3-6}$alkenyloxy, $C_{3-4}$alkynyloxy, $C_{3-6}$cycloalkoxy, $C_{1-6}$alkylcarbonyl-, $C_{1-6}$alkoxycarbonyl, $C_{1-6}$alkyl-S(O)$_w$— (wherein w is 0, 1 or 2), $C_{1-6}$ alkylcarbonyl-N($R^a$)— and $C_{1-6}$alkoxycarbonyl-N($R^a$)— may optionally be substituted by one or more substituents each independently selected from $R^P$; and wherein aryl and heteroaryl may optionally be substituted by one or more substituents each independently selected from $R^f$;

$R^{X1}$ is selected from the group consisting of hydrogen, $C_{1-6}$alkyl and phenyl, or $R^{X1}$ and ring A together with the nitrogen to which they are attached form an 8-10 membered saturated or partially unsaturated bicyclic heterocyclyl which may have one or more additional heteroatoms each independently selected from the group consisting of O, S, and N; wherein the heterocyclyl may optionally be substituted by one, two, three or more substituents each independently selected from the group consisting of $R^{10}$, $-OR^{10}$, $-S(O)_wR^{10}$ (wherein w is 0, 1 or 2), $-N(R^{10})_2$, $-OS(O)_w-R^{10}$ (wherein w is 0, 1, or 2), $-S(O)_w-N(R^{10})_2$ (wherein w is 0, 1 or 2), $-S(O)(NH)R^{10}$, $-P(O)(R^{10})_2$, $-C(O)R^{10}$, $-C(O)N(R^{10})_2$, oxo, halogen and cyano;

$R^{X11}$ is selected from the group consisting of hydrogen, $C_{1-6}$ alkyl and phenyl, or $R^{X11}$ and ring A together with the nitrogen to which they are attached form an 8-10 membered saturated or partially unsaturated bicyclic heterocyclyl which may have one or more additional heteroatoms each independently selected from the group consisting of O, S, and N; wherein the heterocyclyl may optionally be substituted by one, two, three or more substituents each independently selected from the group consisting of $R^{10}$, $-OR^{10}$, $-S(O)_wR^{10}$ (wherein w is 0, 1 or 2), $-N(R^{10})_2$, $-OS(O)_w-R^{10}$ (wherein w is 0, 1, or 2), $-S(O)_w-N(R^{10})_2$ (wherein w is 0, 1 or 2), $-S(O)(NH)R^{10}$, $-P(O)(R^{10})_2$, $-C(O)R^{10}$, $-C(O)N(R^{10})_2$, oxo, halogen and cyano;

$R^{X2}$ and $R^{X3}$ are each independently selected from the group consisting of hydrogen, halogen, hydroxyl, $-NR^aR^b$, $-C(O)-NR^aR^b$, $C_{1-6}$alkyl and $C_{1-6}$alkoxy; wherein $C_{1-6}$alkyl and $C_{1-6}$alkoxy may optionally be substituted by one or more substituents each independently selected from $R^P$;

or $R^{X2}$ and $R^{X3}$ together with the carbon to which they are attached form a 3-6 membered carbocycle optionally substituted by one or more substituents each independently selected from the group consisting of hydrogen, halogen, $-NR^aR^b$, $-C(O)-NR^aR^b$, oxo, $C_{1-6}$alkyl and $C_{1-6}$alkoxy;

$R^{X4}$ and $R^{X5}$ are each independently selected from the group consisting of hydrogen and $C_{1-6}$alkyl; wherein $C_{1-6}$alkyl may optionally be substituted by one or more substituents each independently selected from $R^P$;

$R^{X6}$ and $R^{X7}$ are each independently selected from the group consisting of hydrogen, halogen, $-C(O)-NR^aR^b$, cyano and $C_{1-6}$alkyl; wherein $C_{1-6}$alkyl may optionally be substituted by one or more substituents each independently selected from $R^P$;

$R^Y$ is selected from the group consisting of hydrogen, $C_{1-6}$alkyl and phenyl;

$R^3$ is selected from the group consisting of hydrogen, $C_{1-6}$alkyl and phenyl;

$R^f$ is independently selected, for each occurrence, from the group consisting of $R^P$, $C_{1-6}$alkyl, $C_{3-6}$cycloalkyl, $C_{2-6}$alkenyl, $C_{2-6}$alkynyl, $C_{1-6}$alkoxy, $C_{1-6}$ alkylcarbonyl-, $C_{1-6}$alkoxycarbonyl, $C_{1-6}$alkyl-S(O)$_w$—, (wherein wherein w is 0, 1 or 2), $C_{1-6}$alkylcarbonyl-N(R$^a$)— and $C_{1-6}$alkoxycarbonyl-N(R$^a$)—; wherein $C_{1-6}$alkyl, $C_{3-6}$cycloalkyl, $C_{2-6}$alkenyl, $C_{2-6}$alkynyl, $C_{1-6}$alkoxy, $C_{1-6}$alkylcarbonyl-, $C_{1-6}$alkoxycarbonyl, $C_{1-6}$alkyl-S(O)$_w$—, $C_{1-6}$alkylcarbonyl-N(R$^a$)—, and $C_{1-6}$alkoxycarbonyl-N(R$^a$)— may be optionally substituted by one or more substituents selected from $R^P$;

$R^h$ is independently selected, for each occurrence, from the group consisting of hydrogen, $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkylcarbonyl-, $C_{1-6}$alkoxycarbonyl-, $R^aR^bN$-carbonyl- and $R^aR^bN$—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkylcarbonyl- and $C_{1-6}$alkoxycarbonyl- may optionally be substituted by one or more substituents selected from $R^P$;

$R^a$ and $R^b$ are independently selected, for each occurrence, from the group consisting of hydrogen and $C_{1-6}$alkyl; wherein $C_{1-6}$alkyl may optionally be substituted by one or more substituents selected from halogen, cyano, oxo and hydroxyl;

or $R^a$ and $R^b$, together with the nitrogen to which they are attached, may form a 4-6 membered monocyclic heterocyclic ring, which may have an additional heteroatom selected from the group consisting of O, S, and N; wherein the 4-6 membered heterocyclic ring may optionally be substituted by one or more substituents selected from the group consisting of halogen, cyano, oxo or hydroxyl; and $R^P$ is independently selected, for each occurrence, from the group consisting of halogen, hydroxyl, cyano, $C_{1-6}$alkoxy, $R^aR^bN$—, $R^aR^bN$-carbonyl-, $R^aR^bN$—SO$_2$—, and $R^aR^bN$-carbonyl-N(R$^a$)—.

The disclosure also provides pharmaceutical compositions containing the compounds described herein. Further, the disclosure provides a method of inhibiting SHP2 phosphatase activity in a subject by administering a therapeutically effective amount of a compound or composition described herein, to a subject, e.g., a human, in need.

The disclosure further provides a method of treating a disorder in a subject by administering a therapeutically effective amount of a compound or composition described herein, to a subject in need thereof. Examples of disorders include Noonan syndrome, neutropenia, diabetes, neuroblastoma, melanoma, acute myeloid leukemia, juvenile leukemia, juvenile myelomonocytic leukemia, breast cancer, lung cancer, and colorectal cancer. In addition to the compound or composition described herein, such method may include administration of a therapeutically effective amount of an antibody, an antibody-drug conjugate, an immunomodulator, or a histone deacetylase inhibitor.

The present disclosure is based, in part, on certain discoveries which are described more fully in the Examples section of the present application. For example, the present disclosure is based, in part, on the discovery of compounds of Formula (I) and the SHP2 phosphatase inhibition exhibited by such compounds.

These and other embodiments of the disclosure are further described in the following sections of the application, including the Detailed Description, Examples, and Claims. Still other objects and advantages of the disclosure will become apparent by those of skill in the art from the disclosure herein, which are simply illustrative and not restrictive. Thus, other embodiments will be recognized by the ordinarily skilled artisan without departing from the spirit and scope of the disclosure.

DETAILED DESCRIPTION

Activating SHP2 mutations have been detected in juvenile myelomonocytic leukemia (e.g., Q506P), chronic myelomonocytic leukemia (e.g., Y63C), neuroblastoma (e.g., T507K), melanoma (e.g., R138Q), acute myeloid leukemia (e.g., G503V), breast cancer, lung cancer (e.g., E76V), colorectal cancer (e.g., E76G). (M. Bentires-Alj et al., in Cancer Res. 2004, 64, 8816-8820; and references cited therein.

SHP2 phosphatase inhibitors are disclosed, e.g., in WO 2015/107493; WO 2015/107494; WO 2015/107495; and J.

G. Fortanet et al., in *J. Med. Chem.* 2016, DOI: 10.1021/ acs.jmedchem.6b00680; and references cited therein. The effects of SHP2 phsophatase inhibition are described, e.g., Y.-N. P. Chen et al., in *Nature,* 2016, doi:10.1038/nature18621; J. Wang et al., in *J. Clin. Invest.* 2016, 126, 2077-2092; and references cited therein.

The compounds and/or compositions of the disclosure, alone or in combination with other treatments, may be effective in treating, reducing, and/or suppressing disorders related to SHP2 phosphatase activity such as, e.g., Noonan syndrome, Leopard Syndrome, diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer, esophageal cancer, gastric cancer, squamous-cell carcinoma of the head and neck (SCCHN), neutropenia (Kostmann's syndrome), and systemic lupus erythematosus. See, e.g, N. Aceto et al. *Nature Medicine,* 2012, 28, 529-538; C. M. Furcht et al. *Oncogene,* 2013, 32, 2346-2355; V. E. Schneeberger et al. *Oncotarget,* 2015, 6, 6191-6202; P. Cai et al., *Biomedicine & Pharmacotherapy* 2014, 68, 285-290; and references cited therein.

The method described herein may also include additionally administering a therapeutically effective amount of an antibody, an antibody-drug conjugate, an immunomodulator, or a histone deacetylase inhibitor.

Abbreviations and Definitions

The term "compound of the disclosure" as used herein means a compound of Formula (I). The term is also intended to encompass salts, hydrates, tautomers, stereoisomers, and isotopic substitutions thereof.

The term "composition(s) of the disclosure" as used herein means compositions comprising a compound of the disclosure, and salts thereof. The compositions of the disclosure may further comprise other agents such as, e.g., excipients, stabilants, lubricants, solvents, and the like.

The term "isomer" as used herein refers to a compound having the identical chemical formula but different structural or optical configurations. The term "stereoisomer" as used herein refers to and includes isomeric molecules that have the same molecular formula but differ in positioning of atoms and/or functional groups in the space. All stereoisomers of the present compounds (e.g., those which may exist due to asymmetric carbons on various substituents), including enantiomeric forms and diastereomeric forms, are contemplated within the scope of this disclosure.

The term "tautomer" as used herein refers to one of two or more structural isomers which exist in equilibrium and which are readily converted from one isomeric form to another. It is understood that tautomers encompass valence tautomers and proton tautomers (also known as prototropic tautomers). Valence tautomers include interconversions by reorganization of some of the bonding electrons. Proton tautomers include interconversions via migration of a proton, such as keto-enol and imine-enamine isomerizations.

The term "isotopic substitution" as used herein refers to the substitution of an atom with its isotope. The term "isotope" as used herein refers to an atom having the same atomic number as that of atoms dominant in nature but having a mass number (neutron number) different from the mass number of the atoms dominant in nature. It is understood that a compound with an isotopic substitution refers to a compound in which at least one atom contained therein is substituted with its isotope. Atoms that can be substituted with its isotope include, but are not limited to, hydrogen, carbon, and oxygen. Examples of the isotope of a hydrogen atom include $^2$H (also represented as D) and $^3$H. Examples of the isotope of a carbon atom include $^{13}$C and $^{14}$C. Examples of the isotope of an oxygen atom include $^{18}$O.

The term "alkyl", as used herein, unless otherwise indicated, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, wherein the one or more substituents are independently $C_1$-$C_{10}$ alkyl. Examples of "alkyl" groups include methyl, ethyl, propyl, isopropyl, butyl, iso-butyl, sec-butyl, tert-butyl, pentyl, hexyl, heptyl, cyclopropyl, cyclobutyl, cyclopentyl, cyclohexyl, cycloheptyl, norbornyl, and the like.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur, or a 8-10 membered bicyclic unsaturated or partially unsaturated ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine, tetrahydroquinoline, etc.

The terms "heterocyclyl" or "heterocyclic group" are art-recognized and refer to saturated 4-10 membered monocyclic and bicyclic ring structures, including bridged or fused rings, and whose ring structures include one to three heteroatoms, such as nitrogen, oxygen, and sulfur. Where possible, heterocyclyl rings may be linked to the adjacent radical through carbon or nitrogen.

The term "pharmaceutically acceptable salt" is intended to include salts derived from inorganic or organic acids including, e.g., hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluroacetic, trichloroacetic, naphthalene-2 sulfonic and other acids; and salts derived from inorganic or organic bases including, e.g., sodium, potassium, calcium, magnesium, zinc, ammonia, lysine, arginine, histidine, polyhydroxylated amines or tetrafluoroborate. Exemplary pharmaceutically acceptable salts are found, e.g., in Berge, et al. (*J. Pharm. Sci.* 1977, 66(1), 1; and Gould, P. L., *Int. J. Pharmaceutics* 1986, 33, 201-217; (each hereby incorporated by reference in its entirety). Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifuimarate, and hemisuccinate.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, e.g., to reduce or ameliorate the severity and/or duration of afflictions related to SHP2 phosphatase, or one or more symptoms thereof, prevent the advancement of conditions or symptoms related to afflictions related to SHP2 phosphatase, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. "Treatment" can also mean prolonging survival as compared to expected survival if not receiving treatment.

The phrase "in need thereof" refers to the need for symptomatic or asymptomatic relief from conditions related to SHP2 phosphatase activity or that may otherwise be relieved by the compounds and/or compositions of the disclosure.

In some embodiments, SHP2 phosphatase inhibitors described herein encompass compounds of Formula I, or a pharmaceutically acceptable salt or stereoisomer thereof, wherein Formula I is represented by:

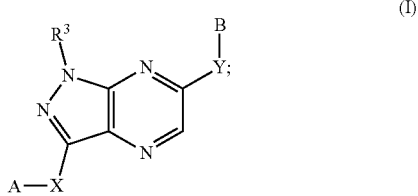

(I)

wherein

X is selected from the group consisting of a bond, —O—, —NR$^1$—, —C(O)NR$^{X11}$—, —S(O)$_w$— (wherein w is 0, 1 or 2), —C(O)—, —C(R$^{X2}$R$^{X3}$)—, —(OC(R$^{X4}$R$^{X5}$)—, —C(R$^{X4}$R$^{X5}$)—O—, —NR$^{X1}$—C(R$^{X4}$R$^{X5}$)—, —C(R$^{X4}$R$^{X5}$)— NR$^{X1}$—, —C═C(R$^{X6}$R$^{X7}$), —C≡C—, and cyclopropyl;

Y is selected from the group consisting of —NR$^Y$—, —C$_{1-3}$alkylene-NR—, and —NR$^Y$—C$_{1-3}$alkylene-;

A is selected from the group consisting of a 6-10 membered monocyclic or bicyclic aryl, a 5-7 membered monocyclic heteroaryl having one or more heteroatoms each independently selected from O, S, or N, a 8-10 membered bicyclic heteroaryl having one or more heteroatoms each independently selected from O, S, or N; and a 4-7 membered heterocyclyl, wherein A may optionally be substituted by one, two, three or more substituents each independently selected from the group consisting of —R$^{10}$, —OR$^{10}$, —S(O)$_w$R$^{10}$ (wherein w is 0, 1 or 2), —N(R$^{10}$)$_2$, —OS(O)$_w$—R$^{10}$ (wherein w is 0, 1, or 2), —S(O)$_w$—N(R$^{10}$)$_2$ (wherein w is 0, 1 or 2), —N(R$^{10}$)—S(O)$_w$—R$^{10}$ (wherein w is 0, 1 or 2), —S(O)$_w$—(NH)R$^{10}$, —N(R$^{10}$)—S(O)—R$^{10}$, —P(O)(R$^{10}$)$_2$, —C(O)R$^{10}$, —C(O)N(R$^{10}$)$_2$, —NR$^{10}$—C(O)R$^{10}$, oxo, halogen and cyano;

R$^{10}$ is independently selected from the group consisting of hydrogen, C$_{1-6}$alkyl, C$_{3-6}$cycloalkyl, C$_{2-6}$heteroalkyl, heterocycloalkyl, aryl, and heteroaryl; wherein C$_{1-6}$alkyl, C$_{3-6}$cycloalkyl, C$_{2-6}$heteroalkyl, heterocycloalkyl, aryl, and heteroaryl may optionally be substituted by one, two, three or more substituents each independently selected from the group consisting of halogen, hydroxyl, —C(O)—R$^{20}$, —C(NR$^a$)—R$^b$, —NR$^a$R$^b$, C$_{1-6}$alkyl, C$_{1-6}$haloalkyl and C$_{1-6}$alkoxy;

R$^{20}$ is selected from the group consisting of hydrogen, hydroxyl, halogen, —NR$^a$R$^b$, C$_{1-6}$alkyl and C$_{1-6}$alkoxy;

B is a 3-7 membered saturated carbocyclic or 4-7 membered saturated heterocyclic ring; wherein the heterocyclic ring B may have one or two heteroatoms each independently selected from the group consisting of O, S(O)$_w$ (wherein w is 0, 1, or 2), and NR$^h$;

carbocyclic or heterocyclic ring B may optionally be substituted on one or more available carbons by one, two, three or more substituents each independently selected from the group consisting of halogen, hydroxyl, cyano, oxo, —NR$^a$R$^b$, —CO$_2$H, —C(O)—NR$^a$R$^b$, —S(O)$_2$—NR$^a$R$^b$, —NR$^a$—S(O)$_2$—C$_{1-6}$alkyl, C$_{1-6}$ alkyl, C$_{2-6}$alkenyl, C$_{2-4}$alkynyl, C$_{3-6}$cycloalkyl, C$_{1-6}$alkoxy, C$_{3-6}$alkenyloxy, C$_{3-4}$alkynyloxy, C$_{3-6}$cycloalkoxy, C$_{1-6}$alkylcarbonyl-, C$_{1-6}$alkoxycarbonyl, C$_{1-6}$alkyl-S(O)$_w$— (wherein w is 0, 1 or 2), C$_{1-6}$alkylcarbonyl-N(R$^a$)—, C$_{1-6}$alkoxycarbonyl-N(R$^a$)—, aryl and heteroaryl; wherein —NR$^a$—S(O)$_2$—C$_{1-6}$alkyl, C$_{1-6}$alkyl, C$_{2-6}$alkenyl, C$_{2-4}$alkynyl, C$_{3-6}$cycloalkyl, C$_{1-6}$ alkoxy, C$_{3-6}$alkenyloxy, C$_{3-4}$alkynyloxy, C$_{3-6}$cycloalkoxy, C$_{1-6}$alkylcarbonyl-, C$_{1-6}$alkoxycarbonyl, C$_{1-6}$alkyl-S(O)$_w$— (wherein w is 0, 1 or 2), C$_{1-6}$alkylcarbonyl-N(R$^a$)— and C$_{1-6}$alkoxycarbonyl-N(R$^a$)— may optionally be substituted by one or more substituents each independently selected from R$^P$; and wherein aryl and heteroaryl may optionally be substituted by one or more substituents each independently selected from R$^r$;

R$^{X1}$ is selected from the group consisting of hydrogen, C$_{1-6}$alkyl and phenyl, or R$^{X1}$ and ring A together with the nitrogen to which they are attached form an 8-10 membered saturated or partially unsaturated bicyclic heterocyclyl which may have one or more additional heteroatoms each independently selected from the group consisting of O, S, and N; wherein the heterocyclyl may optionally be substituted by one, two, three or more substituents each independently selected from the group consisting of R$^{10}$, —OR$^{10}$, —S(O)$_w$R$^{10}$ (wherein w is 0, 1 or 2), —N(R$^{10}$)$_2$, —OS(O)$_w$—R$^{10}$ (wherein w is 0, 1, or 2), —S(O)$_w$—N(R$^{10}$)$_2$ (wherein w is 0, 1 or 2), —S(O)(NH)R$^{10}$, —P(O)(R$^{10}$)$_2$, —C(O)R$^{10}$, —C(O)N(R$^{10}$)$_2$, oxo, halogen and cyano;

R$^{X11}$ is selected from the group consisting of hydrogen, C$_{1-6}$alkyl and phenyl, or R$^{X11}$ and ring A together with the nitrogen to which they are attached form an 8-10 membered saturated or partially unsaturated bicyclic heterocyclyl which may have one or more additional heteroatoms each independently selected from the group consisting of O, S, and N; wherein the heterocyclyl may optionally be substituted by one, two, three or more substituents each independently selected from the group consisting of R$^{10}$, —OR$^{10}$, —S(O)$_w$R$^{10}$ (wherein w is 0, 1 or 2), —N(R$^{10}$)$_2$, —OS $(O)_w$—$R^{10}$ (wherein w is 0, 1, or 2), —$S(O)_w$—$N(R^{10})_2$ (wherein w is 0, 1 or 2), —S(O)(NH)$R^{10}$, —P(O)($R^{10}$)$_2$, —C(O)$R^{10}$, —C(O)N($R^{10}$)$_2$, oxo, halogen and cyano;

$R^{X2}$ and $R^{X3}$ are each independently selected from the group consisting of hydrogen, halogen, hydroxyl, —NR$^a$R$^b$, —C(O)—NR$^a$R$^b$, $C_{1-6}$alkyl and $C_{1-6}$alkoxy; wherein $C_{1-6}$alkyl and $C_{1-6}$alkoxy may optionally be substituted by one or more substituents each independently selected from $R^P$;

or $R^{X2}$ and $R^{X3}$ together with the carbon to which they are attached form a 3-6 membered carbocycle optionally substituted by one or more substituents each independently selected from the group consisting of hydrogen, halogen, —NR$^a$R$^b$, —C(O)—NR$^a$R$^b$, oxo, $C_{1-6}$alkyl and $C_{1-6}$alkoxy;

$R^{X4}$ and $R^{X5}$ are each independently selected from the group consisting of hydrogen and $C_{1-6}$alkyl; wherein $C_{1-6}$alkyl may optionally be substituted by one or more substituents each independently selected from $R^P$;

$R^{X6}$ and $R^{X7}$ are each independently selected from the group consisting of hydrogen, halogen, —C(O)—NR$^a$R$^b$, cyano and $C_{1-6}$alkyl; wherein $C_{1-6}$alkyl may optionally be substituted by one or more substituents each independently selected from $R^P$;

$R^Y$ is selected from the group consisting of hydrogen, $C_{1-6}$alkyl and phenyl;

$R^3$ is selected from the group consisting of hydrogen, $C_{1-6}$alkyl and phenyl;

$R^f$ is independently selected, for each occurrence, from the group consisting of $R^P$, $C_{1-6}$alkyl, $C_{3-6}$cycloalkyl, $C_{2-6}$alkenyl, $C_{2-6}$alkynyl, $C_{1-6}$alkoxy, $C_{1-6}$ alkylcarbonyl-, $C_{1-6}$alkoxycarbonyl, $C_{1-6}$alkyl-S(O)$_w$—, (wherein wherein w is 0, 1 or 2), $C_{1-6}$alkylcarbonyl-N(R$^a$)— and $C_{1-6}$alkoxycarbonyl-N(R$^a$)—; wherein $C_{1-6}$alkyl, $C_{3-6}$cycloalkyl, $C_{2-6}$alkenyl, $C_{2-6}$alkynyl, $C_{1-6}$alkoxy, $C_{1-6}$alkylcarbonyl-, $C_{1-6}$alkoxycarbonyl, $C_{1-6}$alkyl-S(O)$_w$—, $C_{1-6}$alkylcarbonyl-N(R$^a$)—, and $C_{1-6}$alkoxycarbonyl-N(R$^a$)— may be optionally substituted by one or more substituents selected from $R^P$;

$R^h$ is independently selected, for each occurrence, from the group consisting of hydrogen, $C_{1-6}$alkyl, $C_{3-6}$alkenyl, $C_{3-4}$alkynyl, $C_{3-6}$cycloalkyl, $C_{1-6}$alkyl-S(O)$_2$—, $C_{1-6}$alkylcarbonyl-, $C_{1-6}$alkoxycarbonyl-, R$^a$R$^b$N-carbonyl- and R$^a$R$^b$N—SO$_2$—; wherein $C_{1-6}$alkyl, $C_{3-6}$alkenyl, $C_{3-4}$alkynyl, $C_{3-6}$cycloalkyl, $C_{1-6}$alkyl-S(O)$_2$—, $C_{1-6}$ alkylcarbonyl- and $C_{1-6}$alkoxycarbonyl- may optionally be substituted by one or more substituents selected from $R^P$;

$R^a$ and $R^b$ are independently selected, for each occurrence, from the group consisting of hydrogen and $C_{1-6}$alkyl; wherein $C_{1-6}$alkyl may optionally be substituted by one or more substituents selected from halogen, cyano, oxo and hydroxyl;

or $R^a$ and $R^b$, together with the nitrogen to which they are attached, may form a 4-6 membered monocyclic heterocyclic ring, which may have an additional heteroatom selected from the group consisting of O, S, and N; wherein the 4-6 membered heterocyclic ring may optionally be substituted by one or more substituents selected from the group consisting of halogen, cyano, oxo or hydroxyl; and $R^P$ is independently selected, for each occurrence, from the group consisting of halogen, hydroxyl, cyano, $C_{1-6}$alkyl, R$^a$R$^b$N—, R$^a$R$^b$N-carbonyl-, R$^a$R$^b$N—SO$_2$—, and R$^a$R$^b$N-carbonyl-N(R$^a$)—.

In some embodiments, X is selected from the group consisting of a bond, —O—, —S—, and —NR$^{X1}$—. In some embodiments, Y is selected from the group consisting of —NR$^Y$—, —CH$_2$—NR$^Y$—, and —NR$^Y$—CH$_2$—. In an embodiment, for example, Y is selected from the group consisting of —NH—, —N(CH$_3$)—, —N(H)—CH$_2$—, and —N(CH$_3$)—CH$_2$—.

In some embodiments, A is selected from the group consisting of phenyl, pyridyl, quinolinyl, indolyl, and indolinyl, wherein phenyl, pyridyl, quinolinyl, indolyl and indolinyl may optionally be substituted by one, two or three substituents each independently selected from the group consisting of —$R^{10}$, —O$R^{10}$, —S$R^{10}$, —N($R^{10}$)$_2$, —OSO$_2R^{10}$, —SO$_2R^{10}$, —C(O)N($R^{10}$)$_2$, halogen, and cyano. In certain embodiments, A is phenyl; wherein phenyl may optionally be substituted by one, two, or three substituents each independently selected from the group consisting of —O$R^{10}$, halogen, and cyano. In certain other embodiments, A is pyridyl; wherein pyridyl may optionally be substituted by one, two, or three substituents each independently selected from the group consisting of —O$R^{10}$, halogen, and cyano. In an embodiment, $R^{X1}$ and ring A together with the nitrogen to which they are attached form a 1,2,3,4-tetrahydro-1,5-naphthyridine moiety.

In certain embodiments, $R^3$ is selected from the group consisting of hydrogen and CH$_3$.

In some embodiments, A is phenyl, pyridyl, indolyl, or indolinyl, wherein said phenyl, pyridyl, indolyl or indolinyl is optionally substituted with —$R^{10}$, —O$R^{10}$, —S$R^{10}$, —N($R^{10}$)$_2$, —OSO$_2R^{10}$, —SO$_2R^{10}$, —C(O)N($R^{10}$)$_2$, halogen, or cyano.

In some embodiments, A is phenyl, pyridyl, imidazolyl, indolyl, indolinyl, naphthyl, quinolinyl, isoquinolinyl, benzimidazolyl, indazolyl, benzotriazolyl, benzothiazolyl, benzofuranyl, pyrazolopyridyl, quinazolinyl, quinoxalinyl, or cinnolinyl. In some embodiments, A is phenyl. In some embodiments, A is pyridyl. In some embodiments, A is 2-pyridyl. In some embodiments, A is 3-pyridyl. In some embodiments, A is 4-pyridyl. In some embodiments, A is naphthyl. In some embodiments, A is 1-naphthyl. In some embodiments, A is 2-naphthyl. In some embodiments, A is quinolinyl. In some embodiments, A is 2-quinolinyl. In some embodiments, A is 3-quinolinyl. In some embodiments, A is 4-quinolinyl. In some embodiments, A is 5-quinolinyl. In some embodiments, A is 6-quinolinyl. In some embodiments, A is 7-quinolinyl. In some embodiments, A is 8-quinolinyl. In some embodiments, A is isoquinolinyl. In some embodiments, A is 1-isoquinolinyl. In some embodiments, A is 3-isoquinolinyl. In some embodiments, A is 4-isoquinolinyl. In some embodiments, A is 5-isoquinolinyl. In some embodiments, A is 6-isoquinolinyl. In some embodiments, A is 7-isoquinolinyl. In some embodiments, A is 8-isoquinolinyl. In some embodiments, A is indolyl. In some embodiments, A is 2-indolyl. In some embodiments, A is 3-indolyl. In some embodiments, A is 4-indolyl. In some embodiments, A is 5-indolyl. In some embodiments, A is 6-indolyl. In some embodiments, A is 7-indolyl. In some embodiments, A is aryl. In some embodiments, A is bicyclic aryl. In some embodiments, A is heteroaryl. In some embodiments, A is fused bicyclic heteroaryl.

In some embodiments, A is phenyl, pyridyl, or indolyl, wherein said phenyl, pyridyl, or indolyl is optionally substituted with —O$R^{10}$, halogen, or cyano.

In some embodiments, A is phenyl, wherein said phenyl is optionally substituted with —O$R^{10}$, halogen, or cyano.

In some embodiments, A is pyridyl, wherein said pyridyl is optionally substituted with —O$R^{10}$, halogen, or cyano.

In some embodiments, A is indolyl or indolinyl, wherein said indolyl or indolinyl is optionally substituted with —O$R^{10}$, halogen, or cyano.

In some embodiments, A is phenyl, pyridyl, indolyl, or indolinyl, wherein said phenyl, pyridyl, indolyl or indolinyl is optionally substituted with —OR$^{10}$ or halogen.

In some embodiments, A is phenyl, pyridyl, indolyl, or indolinyl, wherein said phenyl, pyridyl, indolyl or indolinyl is optionally substituted with halogen.

In some embodiments, A is phenyl substituted with —R$^{10}$, —OR$^{10}$, —SR$^{10}$, —N(R$^{10}$)$_2$, —OSO$_2$R$^{10}$, —SO$_2$R$^{10}$, —C(O)N(R$^{10}$)$_2$, halogen, or cyano. In some embodiments, A is phenyl substituted with —R$^{10}$. In some embodiments, A is phenyl substituted with —OR$^{10}$. In some embodiments, A is phenyl substituted with —SR$^{10}$. In some embodiments, A is phenyl substituted with —N(R$^{10}$)$_2$. In some embodiments, A is phenyl substituted with —OSO$_2$R$^{10}$. In some embodiments, A is phenyl substituted with —SO$_2$R$^{10}$. In some embodiments, A is phenyl substituted with —C(O)N(R$^{10}$)$_2$. In some embodiments, A is phenyl substituted with halogen. In some embodiments, A is phenyl substituted with cyano.

In some embodiments, A is pyridyl substituted with —R$^{10}$, —OR$^{10}$, —SR$^{10}$, —N(R$^{10}$)$_2$, —OSO$_2$R$^{10}$, —SO$_2$R$^{10}$, —C(O)N(R$^{10}$)$_2$, halogen, or cyano. In some embodiments, A is pyridyl substituted with —R$^{10}$. In some embodiments, A is pyridyl substituted with —OR$^{10}$. In some embodiments, A is pyridyl substituted with —SR$^{10}$. In some embodiments, A is pyridyl substituted with —N(R$^{10}$)$_2$. In some embodiments, A is pyridyl substituted with —OSO$_2$R$^{10}$. In some embodiments, A is pyridyl substituted with —SO$_2$R$^{10}$. In some embodiments, A is pyridyl substituted with —C(O)N(R$^{10}$)$_2$. In some embodiments, A is pyridyl substituted with halogen. In some embodiments, A is pyridyl substituted with cyano.

In some embodiments, A is 3-pyridyl substituted with —OR$^{10}$. In some embodiments, A is 3-pyridyl substituted with —OCH$_3$. In some embodiments, A is 6-methoxypyrid-3-yl. In some embodiments, A is 3-pyridyl substituted with halogen. In some embodiments, A is 3-pyridyl substituted with Cl. In some embodiments, A is 4-chloropyrid-3-yl. In some embodiments, A is 2,3-dichloropyrid-4-yl. In some embodiments, A is 3-chloropyrid-2-yl.

In some embodiments, A is naphthyl substituted with —R$^{10}$, —ORI, —SR$^{10}$, —N(R$^{10}$)$_2$, —OSO$_2$R$^{10}$, —SO$_2$R$^{10}$, —C(O)N(R$^{10}$)$_2$, halogen, or cyano. In some embodiments, A is naphthyl substituted with —R$^{10}$. In some embodiments, A is naphthyl substituted with —OR$^{10}$. In some embodiments, A is naphthyl substituted with —SRI. In some embodiments, A is naphthyl substituted with —N(R$^{10}$)$_2$. In some embodiments, A is naphthyl substituted with —R$^{10}$. In some embodiments, A is naphthyl substituted with —SO$_2$R$^{10}$. In some embodiments, A is naphthyl substituted with —C(O)N(R$^{10}$)$_2$. In some embodiments, A is naphthyl substituted with halogen. In some embodiments, A is naphthyl substituted with cyano.

In some embodiments, A is quinolinyl substituted with —R$^{10}$, —OR$^{10}$, —SR$^{10}$, —N(R$^{10}$)$_2$, —OSO$_2$R$^{10}$, —SO$_2$R$^{10}$, —C(O)N(R$^{10}$)$_2$, halogen, or cyano. In some embodiments, A is quinolinyl substituted with —R$^{10}$. In some embodiments, A is quinolinyl substituted with —OR$^{10}$. In some embodiments, A is quinolinyl substituted with —SR$^{10}$. In some embodiments, A is quinolinyl substituted with —N(R$^{10}$)$_2$. In some embodiments, A is quinolinyl substituted with —OSO$_2$R$^{10}$. In some embodiments, A is quinolinyl substituted with —SO$_2$R$^{10}$. In some embodiments, A is quinolinyl substituted with —C(O)N(R$^{10}$)$_2$. In some embodiments, A is quinolinyl substituted with halogen. In some embodiments, A is quinolinyl substituted with cyano.

In some embodiments, A is isoquinolinyl substituted with —R$^{10}$, —OR$^{10}$, —SR$^{10}$, —N(R$^{10}$)$_2$, —OSO$_2$R$^{10}$, —SO$_2$R$^{10}$, —C(O)N(R$^{10}$)$_2$, halogen, or cyano. In some embodiments, A is isoquinolinyl substituted with —R$^{10}$. In some embodiments, A is isoquinolinyl substituted with —OR$^{10}$. In some embodiments, A is isoquinolinyl substituted with —SR$^{10}$. In some embodiments, A is isoquinolinyl substituted with —N(R$^{10}$)$_2$. In some embodiments, A is isoquinolinyl substituted with —OSO$_2$R$^{10}$. In some embodiments, A is isoquinolinyl substituted with —SO$_2$R$^{10}$. In some embodiments, A is isoquinolinyl substituted with —C(O)N(R$^{10}$)$_2$. In some embodiments, A is isoquinolinyl substituted with halogen. In some embodiments, A is isoquinolinyl substituted with cyano.

In some embodiments, A is indolyl substituted with —R$^{10}$, —OR$^{10}$, —SR$^{10}$, —N(R$^{10}$)$_2$, —OSO$_2$R$^{10}$, —SO$_2$R$^{10}$, —C(O)N(R$^{10}$)$_2$, halogen, or cyano. In some embodiments, A is indolyl substituted with —R$^{10}$. In some embodiments, A is indolyl substituted with —OR$^{10}$. In some embodiments, A is indolyl substituted with —SR$^{10}$. In some embodiments, A is indolyl substituted with —N(R$^{10}$)$_2$. In some embodiments, A is indolyl substituted with —OSO$_2$R$^{10}$. In some embodiments, A is indolyl substituted with —SO$_2$R$^{10}$. In some embodiments, A is indolyl substituted with —C(O)N(R$^{10}$)$_2$. In some embodiments, A is indolyl substituted with halogen. In some embodiments, A is indolyl substituted with cyano.

In some embodiments, A is 1-methyl-1H-indol-4-yl. In some embodiments, A is 1-methyl-1H-indol-3-yl.

In some embodiments, A is imidazol-2-yl. In some embodiments, A is 1-methyl-imidazol-2-yl.

In some embodiments, A is selected from the group consisting of 1,2,3,4-tetrahydroquinoline; 1,2,3,4-tetrahydro-1,5,napthyridine, dihydropyridopyrazine, benzoimidazole, benzoazepine, and dihydropyridooxazine, wherein A is bound to X through an available nitrogen on X; and where A is optionally substituted with one or two substituents each independently selected from halo, CF$_3$, phenyl (optionally substituted with one, two or three halo, C$_{1-3}$alkyl or C$_{1-3}$haloalkyl), C$_{1-3}$alkyl, C$_{1-3}$haloalkyl, and heteroaryl (optionally substituted with one, two or three halo, C$_{1-3}$alkyl or C$_{1-3}$haloalkyl).

In some embodiments, A is selected from the group consisting of

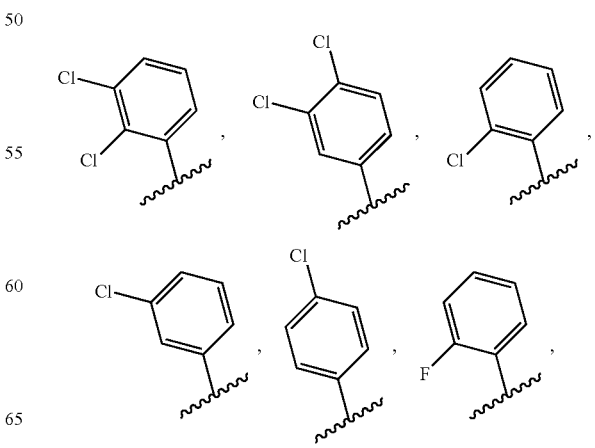

-continued
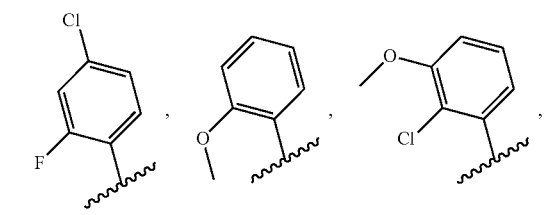
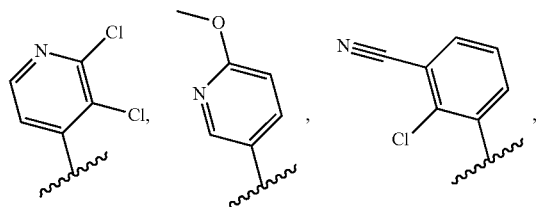
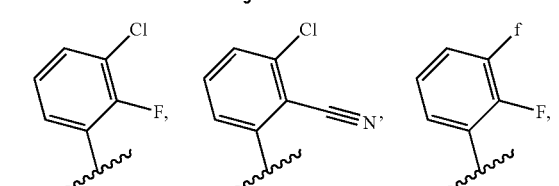
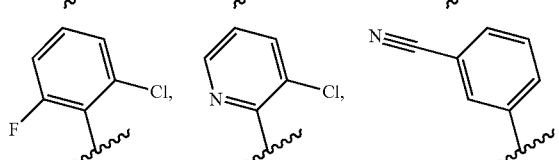
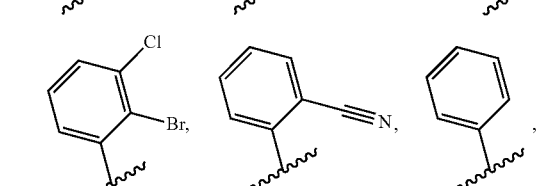
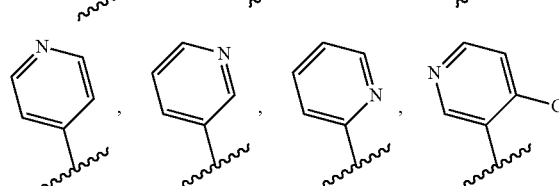
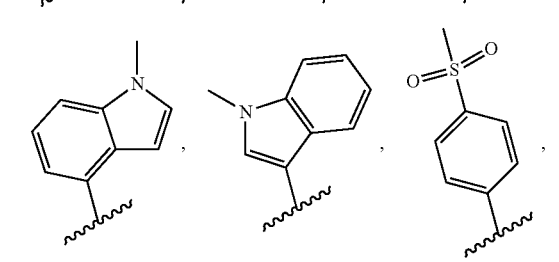
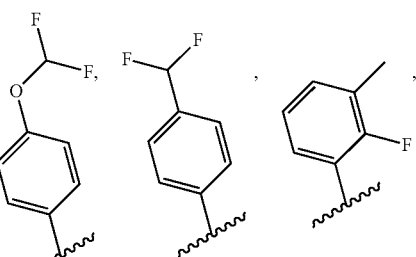
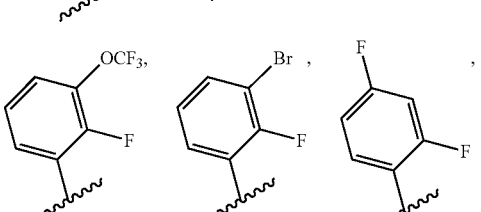
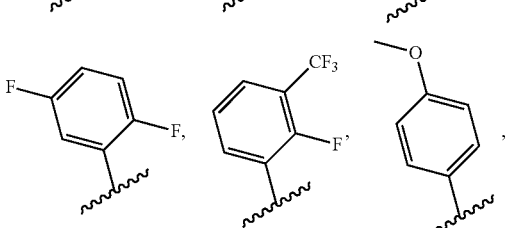
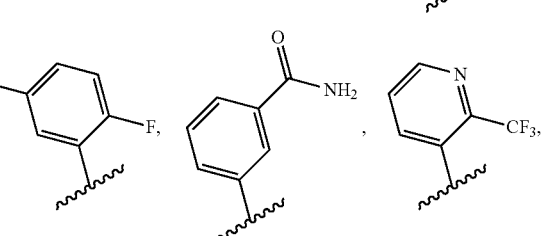
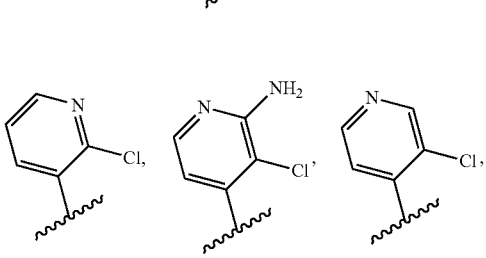
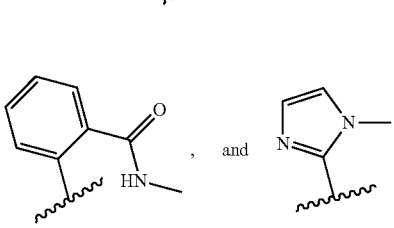
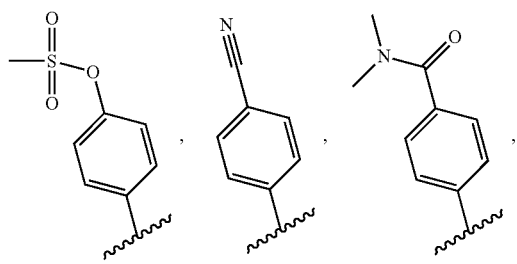
In some embodiments, A is
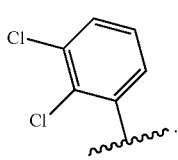.

In some embodiments, A is
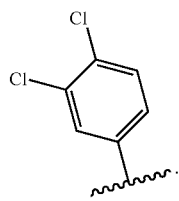 [SMILES: *c1ccc(Cl)c(Cl)c1]
In some embodiments, A is
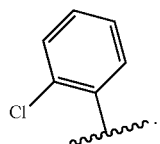
In some embodiments, A is
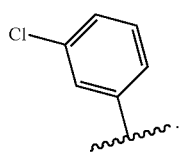 [SMILES: *c1cccc(Cl)c1]
In some embodiments, A is
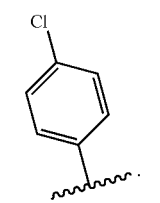 [SMILES: *c1ccc(Cl)cc1]
In some embodiments, A is
In some embodiments, A is
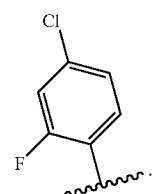
In some embodiments, A is
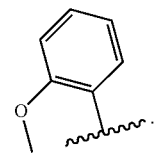 [SMILES: *c1ccccc1OC]
In some embodiments, A is
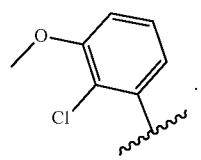 [SMILES: *c1cccc(OC)c1Cl]
In some embodiments, A is
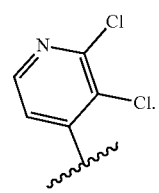 [SMILES: *c1ccnc(Cl)c1Cl]
In some embodiments, A is
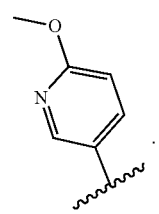
In some embodiments, A is
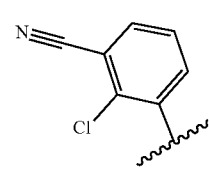
In some embodiments, A is
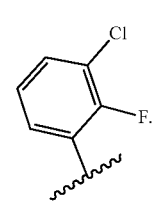 [SMILES: *c1cccc(Cl)c1F]

In some embodiments, A is
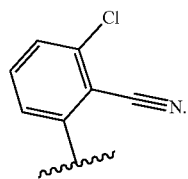
In some embodiments, A is
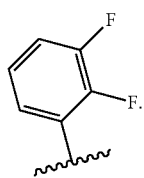
In some embodiments, A is
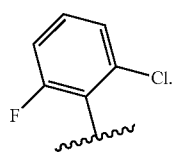
In some embodiments, A is
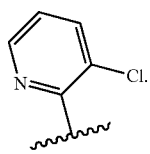 [SMILES: *c1ncccc1Cl]
In some embodiments, A is
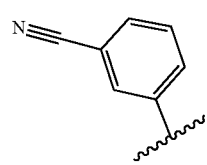
In some embodiments, A is
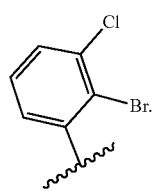 [SMILES: *c1cccc(Cl)c1Br]
In some embodiments, A is
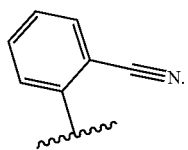 [SMILES: *c1ccccc1C#N]
In some embodiments, A is
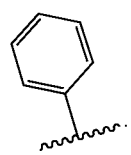 [SMILES: *c1ccccc1]
In some embodiments, A is
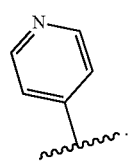
In some embodiments, A is
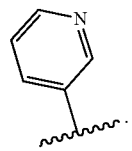
In some embodiments, A is
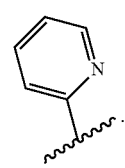
In some embodiments, A is
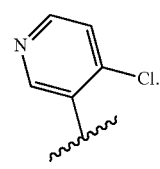

In some embodiments, A is
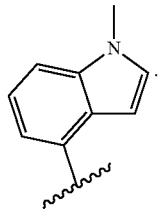 [SMILES: *c1cccc2c1ccn2C]
In some embodiments, A is
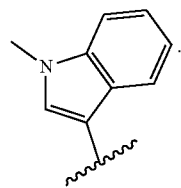 [SMILES: *c1cn(C)c2ccccc12]
In some embodiments, A is
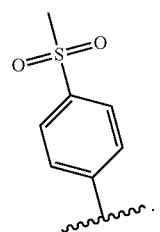
In some embodiments, A is
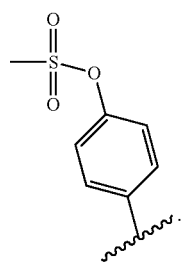 [SMILES: *c1ccc(OS(C)(=O)=O)cc1]
In some embodiments, A is
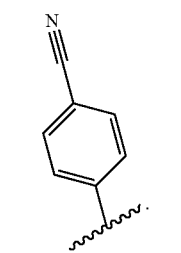 [SMILES: *c1ccc(C#N)cc1]
In some embodiments, A is
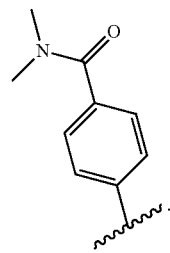 [SMILES: *c1ccc(C(=O)N(C)C)cc1]
In some embodiments, A is
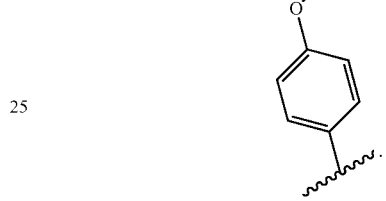
In some embodiments, A is
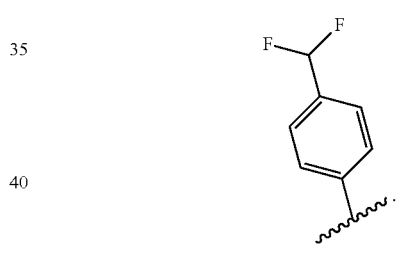
In some embodiments, A is
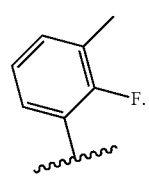 [SMILES: *c1cccc(C)c1F]
In some embodiments, A is
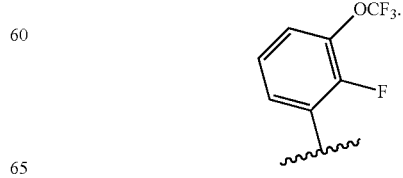

In some embodiments, A is
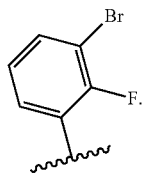
In some embodiments, A is
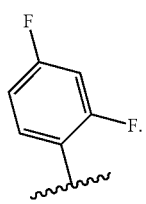 [SMILES: *c1ccc(F)cc1F]
In some embodiments, A is
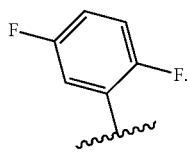
In some embodiments, A is
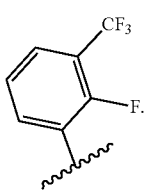 [SMILES: *c1cccc(C(F)(F)F)c1F]
In some embodiments, A is
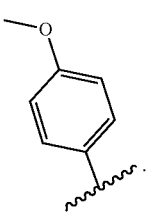 [SMILES: *c1ccc(OC)cc1]
In some embodiments, A is
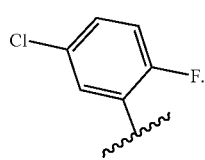 [SMILES: *c1cc(Cl)ccc1F]
In some embodiments, A is
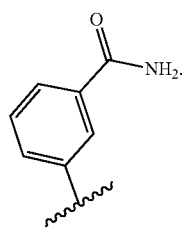 [SMILES: *c1cccc(C(N)=O)c1]
In some embodiments, A is
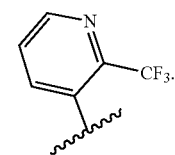 [SMILES: *c1cccnc1C(F)(F)F]
In some embodiments, A is
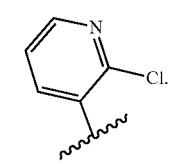 [SMILES: *c1cccnc1Cl]
In some embodiments, A is
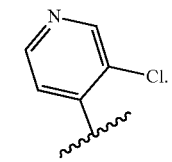 [SMILES: *c1ccncc1Cl]
In some embodiments, A is
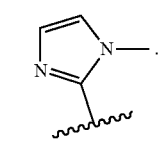
In some embodiments, A is
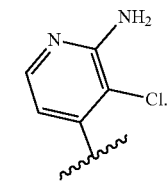 [SMILES: *c1ccnc(N)c1Cl]

In some embodiments, A is

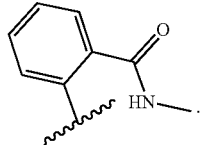 [SMILES: *c1ccccc1C(=O)NC]

In some embodiments, SHP2 phosphatase inhibitors described herein encompass compounds of Formula II, or a pharmaceutically acceptable salt or stereoisomer thereof, wherein Formula II is represented by:

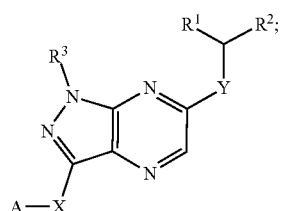

(II)

wherein $R^1$ and $R^2$, together with the carbon to which they are attached, form the 3-7 membered saturated carbocyclic or 4-7 membered saturated heterocyclic ring B; wherein the heterocyclic ring B may have one or two heteroatoms each independently selected from the group consisting of O, $S(O)_w$ (wherein w is 0, 1, or 2), and $NR^h$.

In some embodiments, ring B is cyclopentyl, wherein cyclopentyl may optionally be substituted by one, two, three or more substituents each independently selected from the group consisting of halogen, hydroxyl, cyano, —$NR^aR^b$, —C(O)—$NR^aR^b$, $C_{1-3}$alkyl, and $C_{1-3}$alkoxy; wherein $C_{1-3}$alkyl and $C_{1-3}$alkoxy may optionally be substituted by halogen, hydroxyl and —$NR^aR^b$.

In some embodiments, ring B is cyclohexyl, wherein cyclohexyl may optionally be substituted by one, two, three or more substituents each independently selected from the group consisting of halogen, hydroxyl, cyano, —$NR^aR^b$, —C(O)—$NR^aR^b$, $C_{1-3}$alkyl, and $C_{1-3}$alkoxy; wherein $C_{1-3}$alkyl and $C_{1-3}$alkoxy may optionally be substituted by halogen, hydroxyl and —$NR^aR^b$.

In some embodiments, ring B is tetrahydrofuranyl, wherein tetrahydrofuranyl may optionally be substituted by one, two, three or more substituents each independently selected from the group consisting of halogen, hydroxyl, cyano, —$NR^aR^b$, —C(O)—$NR^aR^b$, $C_{1-3}$alkyl, and $C_{1-3}$alkoxy; wherein $C_{1-3}$alkyl and $C_{1-3}$alkoxy may optionally be substituted by halogen, hydroxyl and —$NR^aR^b$.

In some embodiments, ring B is tetrahydropyranyl, wherein tetrahydropyranyl may optionally be substituted by one, two, three or more substituents each independently selected from the group consisting of halogen, hydroxyl, cyano, —$NR^aR^b$, —C(O)—$NR^aR^b$, $C_{1-3}$alkyl, and $C_{1-3}$alkoxy; wherein $C_{1-3}$alkyl and $C_{1-3}$alkoxy may optionally be substituted by halogen, hydroxyl and —$NR^aR^b$.

In some embodiments, ring B is substituted on an available carbon by a substituent selected from the group consisting of —$NH_2$ and —$CH_2NH_2$. For example, ring B is selected from the group consisting of:

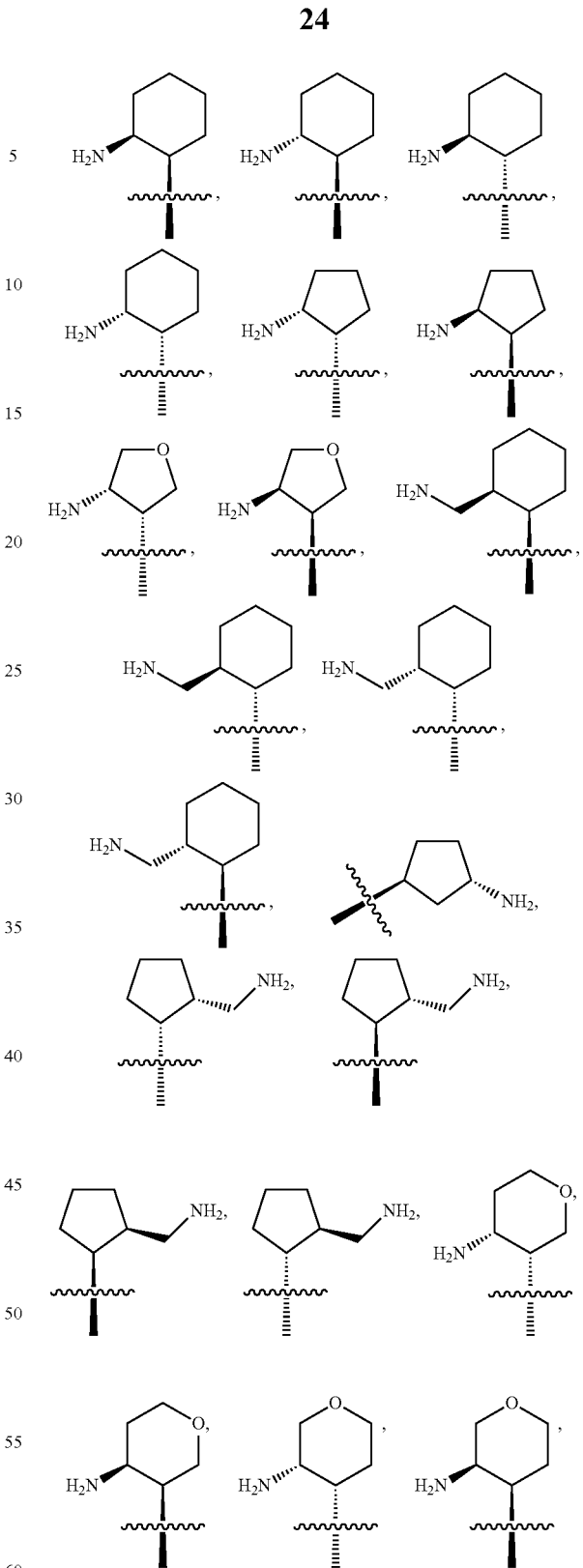

and stereoisomers thereof.

In some embodiments, SHP2 phosphatase inhibitors described herein encompass compounds of Formula III, or a pharmaceutically acceptable salt or stereoisomer thereof, wherein Formula III is represented by:

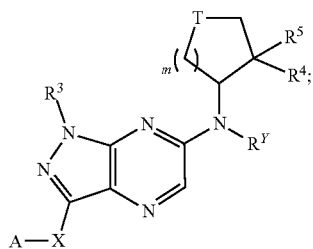

(II)

wherein

X is selected from the group consisting of a bond, —O—, —NR^{X1}—, —S(O)_w— (wherein w is 0, 1 or 2), —C(O)— and —C(R^{X2}R^{X3})—;

A is selected from the group consisting of phenyl, a 5-7 membered monocyclic heteroaryl having one or more heteroatoms each independently selected from O, S, and N, a 8-10 membered bicyclic heteroaryl having one or more heteroatoms each independently selected from the group consisting of O, S, and N, and a 4-7 membered heterocyclyl; wherein A may optionally be substituted by one, two, three or more substituents each independently selected from the group consisting of —R^{10}, —OR^{10}, —N(R^{10})_2, —C(O)N(R^{10})_2, oxo, halogen and cyano;

R^{10} is independently selected from the group consisting of hydrogen, C_{1-6}alkyl, C_{1-6}haloalkyl, C_{3-6}cycloalkyl, heterocycloalkyl, aryl, and heteroaryl, where R^{10} may optionally be substituted by one, two, three or more substituents each independently selected from the group consisting of halogen, —C(O)R^{20}, C_{1-6}alkyl and C_{1-6}haloalkyl;

R^{20} is selected from the group consisting of hydroxyl, halogen, and C_{1-6}alkyl;

R^{X1} is selected from the group consisting of hydrogen, C_{1-6}alkyl and phenyl, or R^{X1} and ring A together with the nitrogen to which they are attached form an 8-10 membered saturated or partially unsaturated bicyclic heterocyclyl which may have one or more additional heteroatoms each independently selected from the group consisting of O, S, and N; wherein the heterocyclyl may optionally be substituted by one, two, three or more substituents each independently selected from the group consisting of R^{10}, —N(R^{10})_2, —C(O)N(R^{10})_2, oxo, halogen and cyano;

R^{X2} and R^{X3} are each independently selected from the group consisting of hydrogen, halogen, hydroxyl, —NR^{a}R^{b}, —C(O)—NR^{a}R^{b}, C_{1-6}alkyl and C_{1-6}alkoxy; or R^{X2} and R^{X3} together with the carbon to which they are attached form a 3-6 membered carbocyclyl which may optionally be substituted by one or more substituents each independently selected from the group consisting of hydrogen, halogen, —NR^{a}R^{b}, —C(O)—NR^{a}R^{b}, oxo, C_{1-6}alkyl and C_{1-6}alkoxy;

R^{Y} is selected from the group consisting of hydrogen, C_{1-6}alkyl and phenyl;

R^{3} is selected from the group consisting of hydrogen, C_{1-6}alkyl and phenyl;

T is selected from the group consisting of —O—, —S(O)_w— (wherein w is 0, 1, or 2), —NR^{h}— and —CH_2—;

R^{4} and R^{5} are each independently selected from the group consisting of hydrogen, halogen, cyano, —NR^{a}R^{b}, —C(O)—NR^{a}R^{b} and C_{1-6}alkyl, wherein C_{1-6}alkyl may optionally be substituted by one, two or three or more substituents each independently selected from the group consisting of halogen, hydroxyl, —NR^{a}R^{b} and oxo;

R^{h} is independently selected, for each occurrence, from the group consisting of hydrogen, C_{1-6}alkyl, C_{14}alkyl-S(O)_2—, C_{1-6}alkylcarbonyl-, C_{1-6}alkoxycarbonyl-, R^{a}R^{b}N-carbonyl- and R^{a}R^{b}N—SO_2—; wherein C_{1-6}alkyl, C_{1-6}alkyl-S(O)_2—, C_{1-6}alkylcarbonyl- and C_{1-6}alkoxycarbonyl- may optionally be substituted by one or more substituents selected from halogen and hydroxyl;

R^{a} and R^{b} are independently selected, for each occurrence, from the group consisting of hydrogen and C_{1-6}alkyl; wherein C_{1-6}alkyl may optionally be substituted by one or more substituents selected from halogen, cyano, oxo and hydroxyl; and m is 0, 1, or 2.

In some embodiments, A is phenyl; wherein phenyl may optionally be substituted by one, two, or three substituents each independently selected from the group consisting of —OR^{10}, halogen, and cyano.

In some embodiments, A is pyridyl; wherein pyridyl may optionally be substituted by one, two, or three substituents each independently selected from the group consisting of —OR^{10}, halogen, and cyano.

In some embodiments, R^{X1} and ring A together with the nitrogen to which they are attached form a 1,2,3,4-tetrahydro-1,5-naphthyridine moiety.

In some embodiments, R^{3} is hydrogen.

In some embodiments, R^{Y} is selected from the group consisting of hydrogen and CH_3.

In some embodiments, R^{1} and R^{5} are independently selected from the group consisting of C_{1-3}alkyl and —NR^{a}R^{b}; wherein C_{1-3}alkyl may optionally be substituted by one, two or three substituents each independently selected from the group consisting of halogen, hydroxyl and —NR^{a}R^{b}. For example, R^{1} and R^{5} are independently selected from the group consisting of —NH_2 and —CH_2NH_2.

In some embodiments, T is selected from the group consisting of —O— and —CH_2—. In a further embodiment, m is 1. In a further embodiment, m is 2.

Examples of compounds of the present disclosure include:

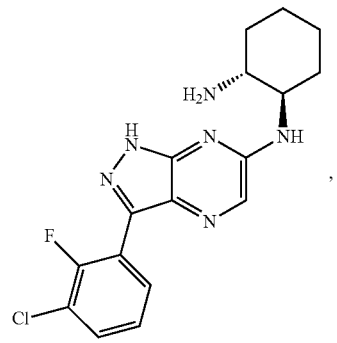

,

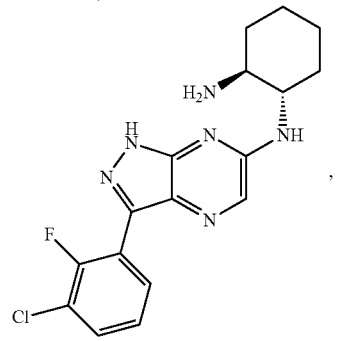

,

-continued

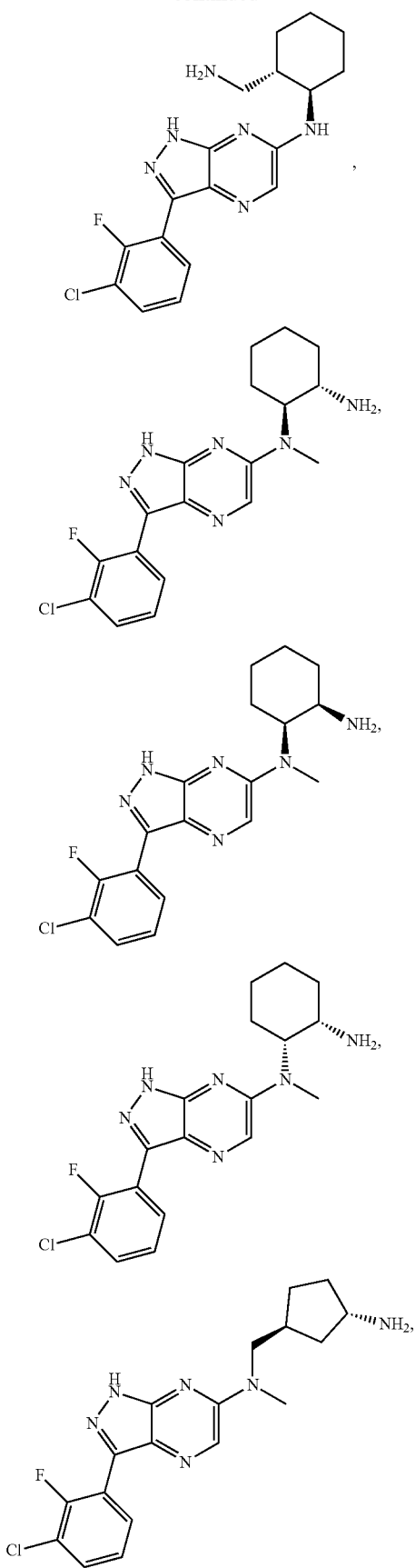
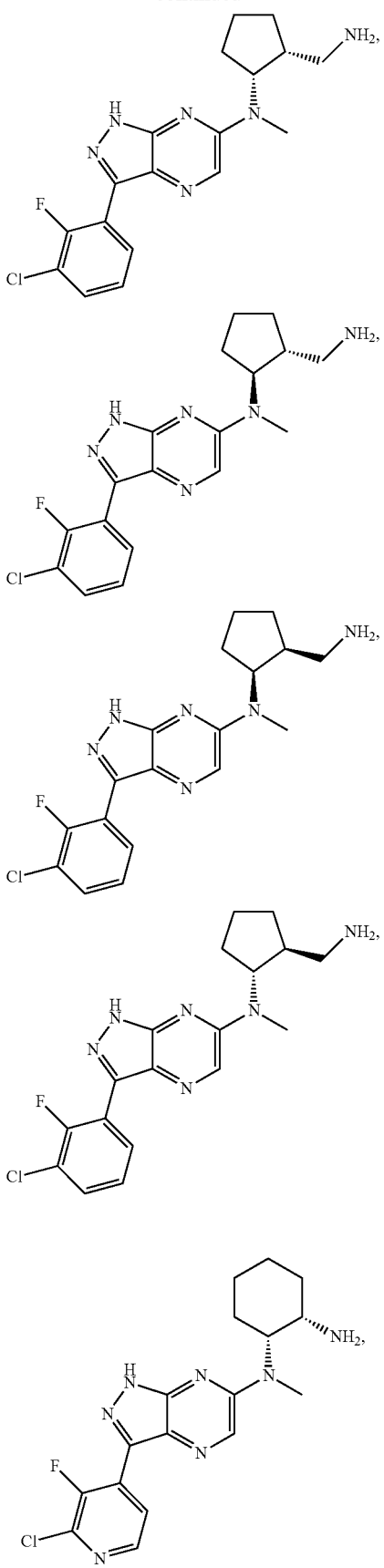

31
-continued
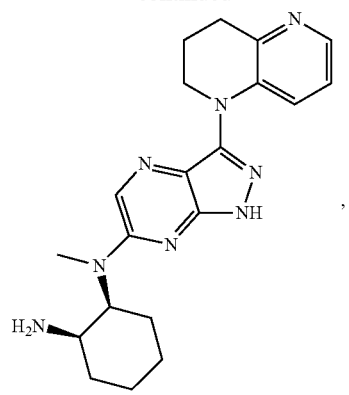
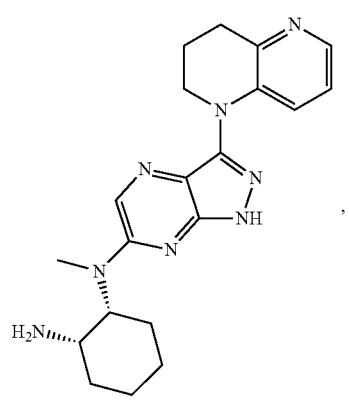
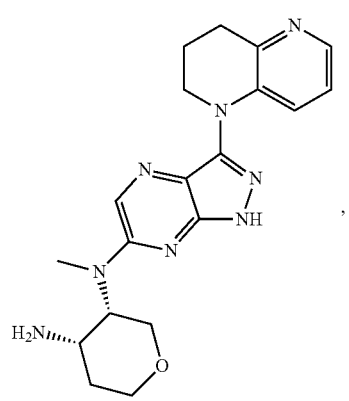
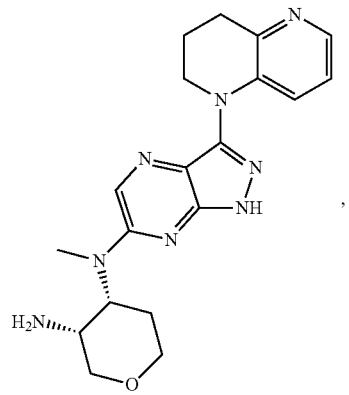
32
-continued
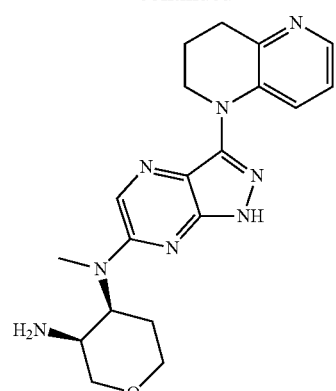
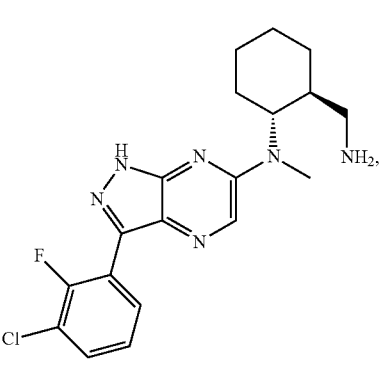
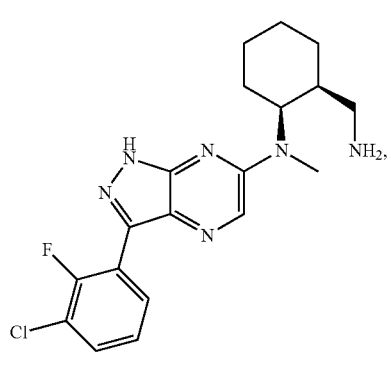
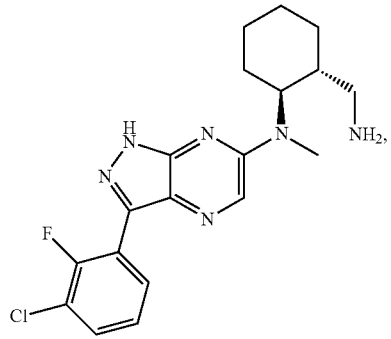

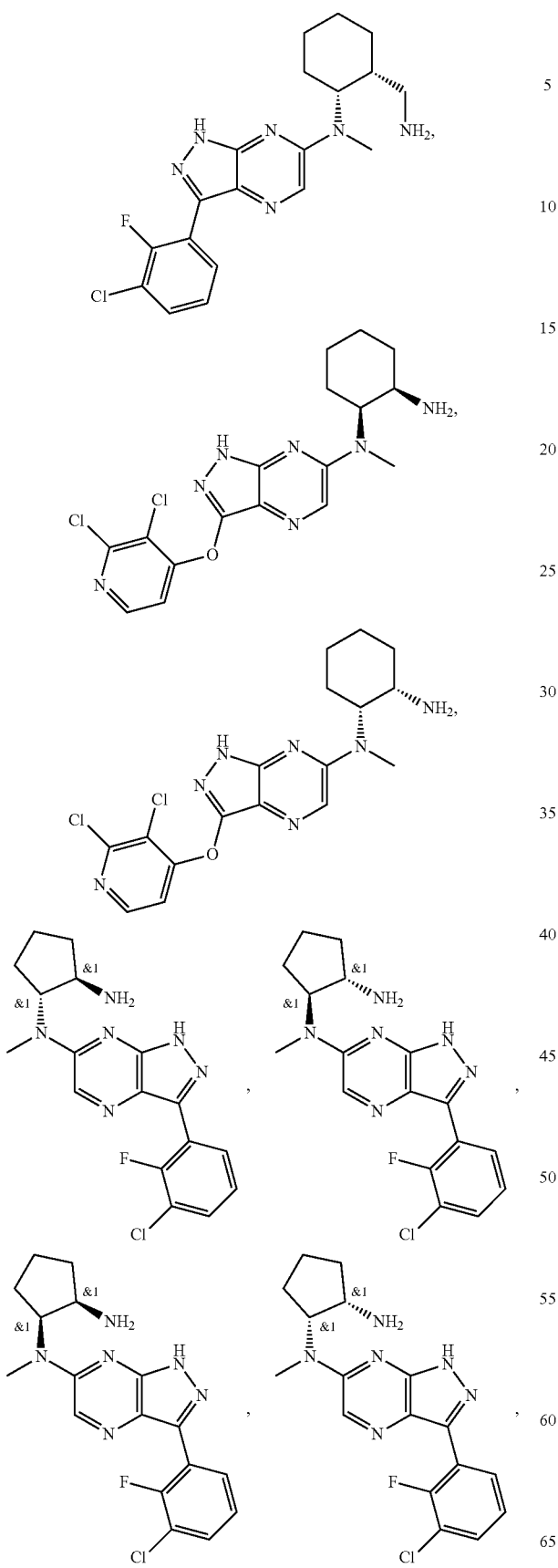
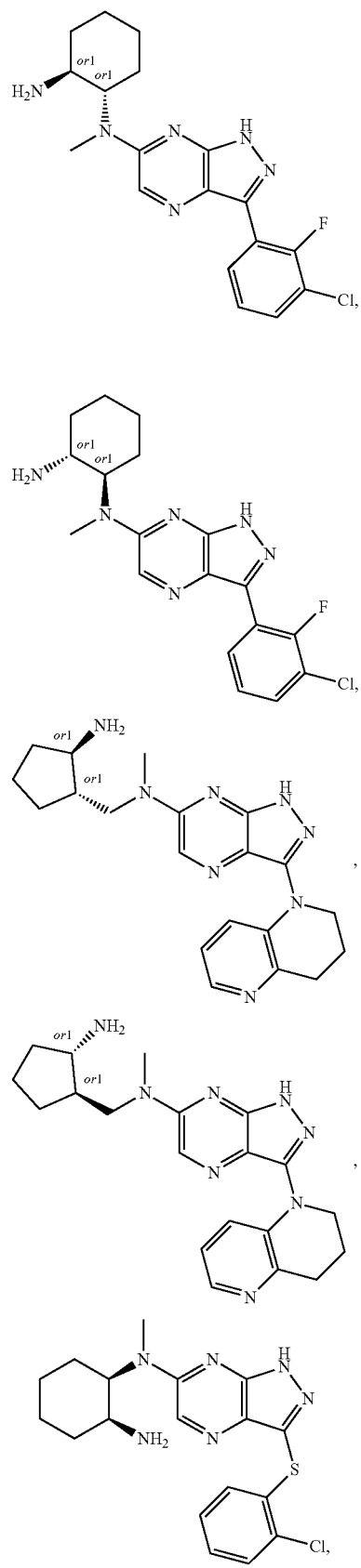

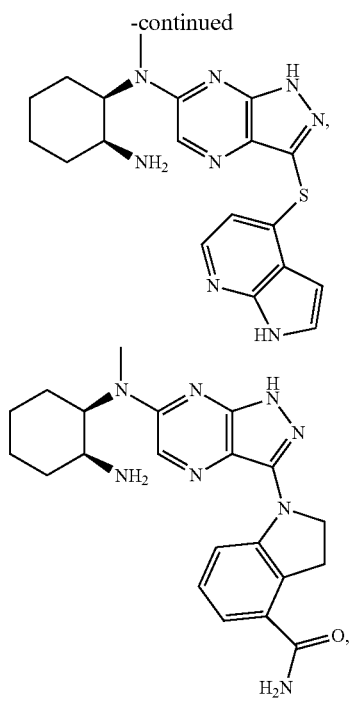

and a pharmaceutically acceptable salt or stereoisomer thereof.

Compounds or compositions of the disclosure can be useful in applications that benefit from inhibition of SHP2 phosphatase enzymes. For example, inhibition of SHP2 phosphatase may offer a therapeutic approach for the treatment of cancer. (See, e.g., Y.-N. P. Chen et al., in *Nature*, 2016, doi:10.1038/nature18621; and references cited therein; each of which hereby incorporated by reference in its entirety.) Inhibition of SHP2 phosphatase also has been found to ameliorate the pathogensis of systemic lupus erythematosus. (See, e.g., J. Wang et al., in *J. Clin. Invest.* 2016, 126, 2077-2092; and references cited therein; each of which hereby incorporated by reference in its entirety.)

In some embodiments, compounds or compositions of the disclosure can be useful in suppressing tumor cell growth. In some embodiments, compounds or compositions of the disclosure can be useful in ameliorating the pathogenesis of systemic lupus erythematosus. In some embodiments, compounds or compositions of the disclosure can be useful in the treatment of various other disorders, including Noonan syndrome (NS), diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer (SW480, SW620, CACO2, HCT116, HT29 colon cancer cell lines), esophageal cancer, gastric cancer, squamous-cell carcinoma of the head and neck (SCCHN), and neutropenia (Kostmann's syndrome).

In some embodiments, compounds or compositions of the disclosure can be used in combination with other treatments and/or cancer therapies. For example, compounds or compositions of the disclosure can be used in combination with, but are not limited to, antibodies, antibody-drug conjugates, kinase inhibitors, immunomodulators, and histone deacetylase inhibitors. The compounds or compositions of the disclosure can also be used in combination with other treatments and/or cancer therapies as disclosed in WO 2015/107495; and references cited therein; each of which is hereby incorporated by reference in its entirety. For example, the compounds disclosed herein (or pharmaceutical compositions containing them) can be used in the treatment of one or more of the diseases mentioned herein, alone or in combination with another therapeutic agent. For example, a compound of formula (I) can be used in combination with the following agents: BCR-ABL inhibitors: imatinib mesylate; inilotinib hydrochloride; nilotinib; dasatinib; bosutinib; ponatinib; bafetinib; danusertib; saracatinib; N-[2-[(1S,4R)-6-[[4-(Cyclobutylamino)-5-(tjifluoromethyl)-2-pyrimidinyl]amino]-1,2,3,4-tetrahydronaphthalen-1,4-imin-9-yl]-2-oxoethyl]-acetamide. ALK inhibitors: crizotinib; 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine, ceritinib, alectinib, brigatinib, entrecinib. BRAF inhibitors: vemurafenib and dabrafenib. FGFR inhibitors: infigratinib, dovitinib, erdafitinib, BLU-554, AZD4547. FLT3 inhibitors: sunitinib malate; midostaurin; tanutinib; sorafenib, lestaurtinib, quizartinib and crenolanib. MEK Inhibitors—trametinib, combimetinib, binimetinib, selumetinib. VEGF receptor inhibitors: bevacizumab, axitinib, Aflibercept, (N-methyl-2-[[3-[(E)-2-pyridin-2-ylethenyl]-1H-indazol-6-yl]sulfanyl]benzamide, brivanib alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, motesanib (N-(2,3-dihydro-3,3-dimethyl-1H-indol-6-yl)-2-[(4-pyridinylmethyl)amino]-3-pyridinecarboxamide, pasireotide, sorafenib. Tyrosine kinase inhibitors: erlotinib hydrochloride, linifanib, sunitinib malate, pazopanib. Epidermal growth factor receptor (EGFR) inhibitors: Gefitnib, osimertinib, cetuximab, panitumumab. HER2 receptor inhibitors: trastuzumab, neratinib, lapatinib or lapatinib ditosylate. MET inhibitors: crizotinib, cabozantinib. CD20 antibodies: rituximab, tositumomab, ofatumumab. DNA Synthesis inhibitors: capecitabine, gemcitabine hydrochloride, nelarabine, hydroxycarbamide. Antineoplastic agents: oxaliplatin. HER dimerization inhibitors: pertuzumab. Human Granulocyte colony-stimulating factor (G-CSF) modulators: Filgrastim. Immunomodulators: Afutuzumab, lenalidomide, thalidomide. CD40 inhibitors: Dacetuzumab. Pro-apoptotic receptor agonists (PARAs): Dulanermin. Heat Shock Protein (HSP) inhibitors: Tanespimycin (17-allylamino-17-demethoxygeldanamycin). Hedgehog antagonists: 2-chloro-N-[4-chloro-3-(2-pyridinyl)phenyl]-4-(methylsulfonyl)-benzamide. Proteasome inhibitors: Bortezomib. PI3K inhibitors: 4-[2-(1H-Indazol-4-yl)-6-[[4-(methylsulfonyl)piperazin-1-yl]methyl]thieno[3,2-d]pyrimidin-4-yl]mo choline, 2-Methyl-2-[4-[3-methyl-2-oxo-8-(quinolin-3-yl)-2,3-dihydroimidazo[4,5-c]quinolin-1-yl]phenyl]propiocyano, buparlisib, taselisib, idelalisib, duvelisib, TGR 1202. Phospholipase A2 inhibitors: Anagrelide. BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl] amino]-3-[(trifluoromethyl)sulfonyl]phenyl]sulfonyl]benzamide. Mitogen-activated protein kinase kinase (MEK) inhibitors: XL-518. Aromatase inhibitors: Exemestane, letrozole, anastrozole, faslodex, tamoxifen. Topoisomerase I inhibitors: Irinotecan, topotecan hydrochloride. Topoisomerase II inhibitors: etoposide, teniposide. mTOR inhibitors: Temsirolimus, ridaforolimus, everolimus. Osteoclastic bone resorption inhibitors: 1-Hydroxy-2-imidazol-1-yl-phosphonoethyl) phosphonic acid monohydrate. CD33 Antibody Drug Conjugates: Gemtuzumab ozogamicin. CD22 Antibody Drug Conjugates: Inotuzumab ozogamicin. CD20 Antibody Drug Conjugates: Ibritumomab tiuxetan. Somatostatin analogs: octreotide. Synthetic Interleukin-11 (IL-11): oprelvekin. Synthetic erythropoietin: Darbepoetin alfa. Receptor Activator for Nuclear Factor κ B (RANK) inhibitors: Denosumab. Tbrombopoietin mimetic peptides: Romiplostim. Cell growth stimulators: Palifermin. Anti-Insulin-like Growth Factor-1 receptor (IGF-1R) antibodies: Figitumumab. Anti-CSl antibodies: Elotuzumab. CD52 antibodies: Alemtuzumab. CTLA-4 inhibitors: Tremelimumab, ipilimumab. PD1 inhibitors: Nivolumab; pembrolizumab; an immunoadhesin; Pidilizumab; and AMP-224. PDL 1 inhibitors: MSB0010718C; YW243.55.S70, MPDL3280A; MEDI-4736, MSB-0010718C, or MDX-1105. LAG-3 inhibitors: BMS-986016. GITR agonists: GITR fusion proteins and anti-GITR antibodies. Histone deacetylase inhibitors (HDI): Voninostat. Anti-CTLA4 antibodies: Tremelimumab; and Ipilimumab. Alkylating agents: Temozolomide, dactinomycin, melphalan, altretamine carmustine, bendamustine, busulfan, carboplatin, lomustine, cisplatin, chlorambucil, cyclophosphamide, dacarbazine, altretamine, ifosfamide, procarbazine, mechlorethamine, mustine and mechloroethamine hydrochloride, streptozocin, thiotepa. Biologic response modifiers: bacillus calmette-guerin, denileukin diftitox. Anti-tumor antibiotics: doxorubicin, bleomycin, daunorubicin, daunorubicin liposomal, mitoxantrone, epirubicin, idarubicin, mitomycin C. Anti-microtubule agents: Estramustine. Cathepsin K inhibitors: Odanacatib. Epothilone B analogs: Ixabepilone. TpoR agonists: Eltrombopag. Anti-mitotic agents: Docetaxel. Adrenal steroid inhibitors: aminoglutethimide. Anti-androgens: Nilutamide, Androgen Receptor inhibitors: enzalutamide, abiraterone acetate, orteronel, galeterone, and seviteronel, bicalutamide, flutamide. Androgens: Fluoxymesterone. CDK1 inhibitors: Alvocidib, palbociclib, ribociclib, trilaciclib, abemaciclib. Gonadotropin-releasing hormone (GnRH) receptor agonists: Leuprolide or leuprolide acetate. Taxane anti-neoplastic agents: Cabazitaxel (1-hydroxy^, 10-dimethoxy-9-oxo-5,20-epoxytax-11-ene-2a,4,13a-triyl-4-acetate-2-benzoate-13-[(2R,3S)-3-{[(tert-butoxy)carbonyl] amino}-2-hydroxy-3-phenylpropanoate), larotaxel ((2α,3ξ, 4α,5β,7α,10β,13α)-4,10-bis(acetyloxy)-13-({(2R,3S)-3-[(tert-butoxycarbonyl) amino]-2-hydroxy-3-phenylpropanoyl}oxy)-1-hydroxy-9-oxo-5,20-epoxy-7,19-cyclotax-11-en-2-yl benzoate). 5HT1a receptor agonists: Xaliproden (also known as SR57746, 1-[2-(2-naphthyl) ethyl]-4-[3-(trifluoromethyl)phenyl]-1,2,3,6-tetrahydropyridine. HPC vaccines: Cervarix® sold by GlaxoSmithKline, Gardasil® sold by Merck; Iron Chelating agents: Deferasinox. Anti-metabolites: Claribine (2-chlorodeoxyadenosine), 5-fluorouracil, 6-thioguanine, pemetrexed, cytarabine, cytarabine liposomal, decitabine, hydroxyurea, fludarabine, floxuridine, cladribine, methotrexate, pentostatin. Bisphosphonates: Pamidronate. Demethylating agents: 5-azacitidine, decitabine. Plant Alkaloids: Paclitaxel protein-bound; vinblastine, vincristine, vinorelbine, paclitaxel. Retinoids: Alitretinoin (sold under the tradename Panretin®), tretinoin (all-trans retinoic acid, also known as ATRA, sold under the tradename Vesanoi®), Isotretinoin (13-cis-retinoic acid, sold under the tradenames Accutane®, Amnesteem®, Claravis®, Claras®, Decutan®, Isotane®, Izotech®, Oratane®, Isotret®, and Sotret®), bexarotene (sold under the tradename Targretin®). Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Corteft, Hydrocort Acetate® and Lanacort®), dexamethazone ((8S,9R,10S,11S,13S,14S,16R,17R)-9-fluoro-11,17-dihydroxy-17-(2-hydroxy acetyl)-10,13,16-trimethyl-6,7,8,9,10,11,12,13, 14,15, 16, 17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®). Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®). Estrogen receptor downregulators: Fulvestrant (sold under the tradename Faslodex®). Anti-estrogens: tamoxifen (sold under the tradename Novaldex®). Toremifene (sold under the tradename Fareston®). Selective estrogen receptor modulators (SERMs): Raloxifene (sold under the tradename Evista®). Leutinizing hormone releasing hormone (LHRH) agonists: Goserelin (sold under the tradename Zoladex®); Progesterones: megestrol (also known as megestrol acetate, sold under the tradename Megace®); Miscellaneous cytotoxic agents: Arsenic trioxide (sold under the tradename Trisenox®), asparaginase (also known as L-asparaginase, Erwinia L-asparaginase, sold under the tradenames Elspar® and Kidrolase®). Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorun factor and folinic acid). Immune checkpoint inhibitors: The term "immune checkpoints" refers to a group of molecules on the cell surface of CD4 and CD8 T cells. Immune checkpoint molecules include, but are not limited to, Programmed Death 1 (PD-1), Cytotoxic T-Lymphocyte Antigen 4 (CTLA-4), B7H1, B7H4, OX-40, CD 137, CD40, and LAG3. Immunotherapeutic agents which can act as immune checkpoint inhibitors useful in the methods of the present disclosure, include, but are not limited to, inhibitors of PD-L1, PD-L2, CTLA4, TIM3, LAG3, VISTA, BTLA, TIGIT, LAIR1, CD 160, 2B4 and/or TGFR beta.

The compounds described herein can function as allosteric inhibitors and block the activation of SHP2 by targeting the auto-inhibited conformation of SHP2.

The compounds described herein can also inhibit SHP2 function through incorporation into agents that catalyze the destruction of SHP2. For example, the compounds can be incorporated into proteolysis targeting chimeras (PROTACs). A PROTAC is a bifunctional molecule, with one portion capable of engaging an E3 ubiquitin ligase, and the other portion having the ability to bind to a target protein meant for degradation by the cellular protein quality control machinery. Recruitment of the target protein to the specific E3 ligase results in its tagging for destruction (i.e., ubiquitination) and subsequent degradation by the proteasome. Any E3 ligase can be used. The portion of the PROTAC that engages the E3 ligase is connected to the portion of the PROTAC that engages the target protein via a linker which consists of a variable chain of atoms. Recruitment of SHP2 to the E3 ligase will thus result in the destruction of the SHP2 protein. The variable chain of atoms can include, for example, rings, heteroatoms, and/or repeating polymeric units. It can be rigid or flexible. It can be attached to the two portions described above using standard techniques.

The compounds described herein can be linked to one end of a variable chain, while the other end of the variable chain can be bound to the E3 ligase. Recruitment of SHP2 to the ligase will thus result in the destruction of the SHP2 protein.

In some embodiments, compounds or compositions of the disclosure can be used in combination with an antibody. In some embodiments, compounds or compositions of the disclosure can be used in combination with an antibody-drug conjugate. In some embodiments, compounds or compositions of the disclosure can be used in combination with a kinase inhibitor. In some embodiments, compounds or compositions of the disclosure can be used in combination with an immunomodulator. In some embodiments, compounds or compositions of the disclosure can be used in combination with a histone deacetylase inhibitor.

In some embodiments, compounds of Formula (I) can be administered to a subject in need of treatment at dosages ranging from about 0.0001 mg to about 100 mg/kg body weight of the subject to be treated per day, such as from about 1.0 to 10 mg/kg. However, additional variations are within the scope of the disclosure.

The compound of Formula (I) can be administered alone or in combination with pharmaceutically acceptable carriers, such as diluents, fillers, aqueous solution, and even organic solvents. The compound and/or compositions of the disclosure can be administered as a tablet, powder, lozenge, syrup, injectable solution, and the like. Additional ingredients, such as flavoring, binder, excipients, and the like are within the scope of the disclosure.

In some embodiments, pharmaceutically acceptable compositions can contain a compound of Formula (I) and/or a pharmaceutically acceptable salt thereof at a concentration ranging from about 0.01 to about 2.0 wt %, such as 0.01 to about 1 wt % or about 0.05 to about 0.5 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

In some embodiments, the present disclosure provides for the use of pharmaceutical compositions and/or medicaments comprised of a compound of Formula (I), or a pharmaceutically acceptable salt thereof, in a method of treating a disease state, and/or condition caused by or related to SHP2 phosphatase. For example, provided herein are methods of treating subjects in need thereof (e.g., subjects suffering from cancer (e.g., leukemia, breast, lung and/or colorectal cancer) an effective amount of a disclosed compound, and optionally an effective amount of an additional compound (e.g., therapeutic agent) such as disclosed herein.

In some embodiments, the method of treatment comprises the steps of: i) identifying a subject in need of such treatment; (ii) providing a compound of Formula (I), or a pharmaceutically acceptable salt thereof; and (iii) administering said compound of Formula (I) in a therapeutically effective amount to treat, suppress and/or prevent the disease state or condition in a subject in need of such treatment.

In some embodiments, the method of treatment comprises the steps of: i) identifying a subject in need of such treatment; (ii) providing a composition comprising a compound of Formula (I), or a pharmaceutically acceptable salt thereof; and (iii) administering said composition in a therapeutically effective amount to treat, suppress and/or prevent the disease state or condition in a subject in need of such treatment.

In some embodiments, the subject is an animal. Animals include all members of the animal kingdom, but are not limited to humans, mice, rats, cats, monkeys, dogs, horses, and swine. In some embodiments, the subject is a human. In some embodiments, the subject is a mouse, a rat, a cat, a monkey, a dog, a horse, or a pig.

In some embodiments, the compound or composition is administered orally. In some embodiments, the compound or composition is administered intravenously.

In some embodiments, the methods comprise administering to the subject an effective amount of a compound of Formula (I), or a pharmaceutically acceptable salt thereof; or a composition comprising a compound of Formula (I), or a pharmaceutically acceptable salt thereof, and a pharmaceutically acceptable carrier.

Pharmaceutically acceptable carriers are well-known to those skilled in the art, and include, e.g., adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient. Often, the pharmaceutically acceptable carrier is chemically inert toward the active compounds and is non-toxic under the conditions of use. Examples of pharmaceutically acceptable carriers may include, e.g., water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in e.g., Remington's: The Science and Practice of Pharmacy, 22nd Ed. (Allen, Loyd V., Jr ed., Pharmaceutical Press (2012)); Modern Pharmaceutics, $5^{th}$ Ed. (Alexander T. Florence, Juergen Siepmann, CRC Press (2009)); Handbook of Pharmaceutical Excipients, $7^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

In some embodiments, the method of treatment, prevention and/or suppression of a condition related to SHP2 phosphatase comprises the steps of: i) identifying a subject in need of such treatment; (ii) providing a compound of Formula (I), or a pharmaceutically acceptable salt thereof; or a composition comprising a compound of Formula (I), or a pharmaceutically acceptable salt thereof, and a pharmaceutically acceptable carrier; and (iii) administering said compound or composition in a therapeutically effective amount to treat, prevent and/or suppress the disease state or condition related to SHP2 phosphatase in a subject in need of such treatment.

In some embodiments, the compounds of the disclosure are formulated into pharmaceutical compositions for administration to subjects in a biologically compatible form suitable for administration in vivo. According to another aspect, the present disclosure provides a pharmaceutical composition comprising a compound of Formula I in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, e.g., detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sufate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula N*R'R"R'"R""Y$^-$, in which the R radicals are identical or different optionally hydroxylated hydrocarbon radicals and Y$^-$ is an anion of a strong acid, such as halide, sulfate and sulfonate anions; cetyltrimethylammonium bromide is one of the cationic surfactants which can be used, amine salts of formula N+R'R"R'", in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

When administered to a subject, the compound of Formula I and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present disclosure are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds and/or compositions of the present disclosure are administered to a human or animal subject by known procedures including oral administration, sublingual or buccal administration. In some embodiments, the compound and/or composition is administered orally.

For oral administration, a formulation of the compounds of the disclosure may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, e.g., sweetening agents such as fructose, aspartame or saccharin; flavoring agents such as peppermint, oil of wintergreen, or cherry; coloring agents; and preservative agents, to provide a pharmaceutically palatable preparation.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

In accordance with the methods of the present disclosure, the compounds of the disclosure are administered to the subject in a therapeutically effective amount, e.g., to reduce or ameliorate symptoms related to SHP2 phosphatase activity in the subject. This amount is readily determined by the skilled artisan, based upon known procedures, including analysis of titration curves established in vivo and methods and assays disclosed herein.

In some embodiments, the methods comprise administration of a therapeutically effective dosage of the compounds of the disclosure. In some embodiments, the therapeutically effective dosage is at least about 0.0001 mg/kg body weight, at least about 0.001 mg/kg body weight, at least about 0.01 mg/kg body weight, at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the therapeutically effective dosage is in the range of about 0.1 mg to about 10 mg/kg body weight, about 0.1 mg to about 6 mg/kg body weight, about 0.1 mg to about 4 mg/kg body weight, or about 0.1 mg to about 2 mg/kg body weight.

In some embodiments the therapeutically effective dosage is in the range of about 1 to 500 mg, about 2 to 150 mg, about 2 to 120 mg, about 2 to 80 mg, about 2 to 40 mg, about 5 to 150 mg, about 5 to 120 mg, about 5 to 80 mg, about 10 to 150 mg, about 10 to 120 mg, about 10 to 80 mg, about 10 to 40 mg, about 20 to 150 mg, about 20 to 120 mg, about 20 to 80 mg, about 20 to 40 mg, about 40 to 150 mg, about 40 to 120 mg or about 40 to 80 mg.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration, and should be decided according to the judgment of the practitioner and each subject's circumstances. In specific embodiments of the disclosure, suitable dose ranges for oral administration of the compounds of the disclosure are generally about 1 mg/day to about 1000 mg/day. In some embodiments, the oral dose is about 1 mg/day to about 800 mg/day. In some embodiments, the oral dose is about 1 mg/day to about 500 mg/day. In some embodiments, the oral dose is about 1 mg/day to about 250 mg/day. In some embodiments, the oral dose is about 1 mg/day to about 100 mg/day. In some embodiments, the oral dose is about 5 mg/day to about 50 mg/day. In some embodiments, the oral dose is about 5 mg/day. In some embodiments, the oral dose is about 10 mg/day. In some embodiments, the oral dose is about 20 mg/day. In some embodiments, the oral dose is about 30 mg/day. In some embodiments, the oral dose is about 40 mg/day. In some embodiments, the oral dose is about 50 mg/day. In some embodiments, the oral dose is about 60 mg/day. In some embodiments, the oral dose is about 70 mg/day. In some embodiments, the oral dose is about 100 mg/day. It will be recognized that any of the dosages listed herein may constitute an upper or lower dosage range, and may be combined with any other dosage to constitute a dosage range comprising an upper and lower limit.

Any of the compounds and/or compositions of the disclosure may be provided in a kit comprising the compounds and/or compositions. Thus, in some embodiments, the compound and/or composition of the disclosure is provided in a kit.

Those skilled in the art will recognize, or be able to ascertain using no more than routine experimentation, many equivalents to the specific embodiments of the disclosure described herein. Such equivalents are intended to be within the scope of the present disclosure.

The disclosure is further described by the following non-limiting Examples.

EXAMPLES

Examples are provided below to facilitate a more complete understanding of the disclosure. The following examples serve to illustrate the exemplary modes of making and practicing the disclosure. However, the scope of the disclosure is not to be construed as limited to specific embodiments disclosed in these Examples, which are illustrative only.

Instrumentation and Methods:

Reactions were monitored and final products were characterized using one of the following methods. LCMS standard conditions were: Waters HPLC system equipped with an Alliance 2695 main module, Waters 996 diode array detector and ZQ micromass ESI-MS detector. Mobile phase A: $H_2O$ (10.0 mM $NH_4HCO_2$), mobile phase B: $CH_3CN$. HPLC conditions were: XBridge C18 column, 4.6×30 mm, 3.5 μm, 0.0-0.2 min. isocratic (5% B), 0.2-2.0 min. gradient (5-100% B), 3.0-3.0 min. isocratic (100% B); flow rate: 3.0 mL/min; UV channel: 254 nm.

Purification of some racemic products was performed using semi preparative HPLC A, semi preparative HPLC B, or semi preparative SFC. Semi preparative HPLC A: Gilson 215 system equipped with a Waters 996 diode array detector and a Waters 2525 pump. Semi preparative HPLC B: Waters 2767 system equipped with a Waters 996 diode array detector, 2× Waters 515 pumps, a Waters 2525 pump and a ZQ micromass ESI-MS detector. Semi preparative SFC: Mettler Toledo Minigram SFC equipped with a Knauer K-2501 UV detector and an Alcott Model 1719 Autosampler.

Product homogeneity and enantiomeric excess determination were performed using Analytical HPLC A: Agilent 1100 HPLC system equipped with an Agilent G1315A diode array detector.

The characterization of compounds disclosed herein is shown below.

| Example | Structure | Proton NMR | LCMS |
|---|---|---|---|
| 1 | 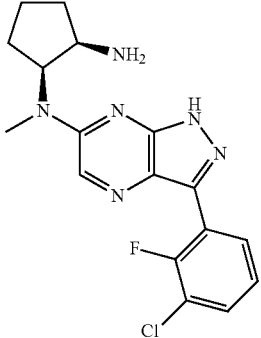<br>single diastereomer, racemic mixture of enantiomers | $^1$H NMR (400 MHz, CD$_3$OD): δ 8.41 (s, 1H), 8.05-8.01 (m, 1H), 7.61-7.57 (m, 1H), 7.34 (t, J = 8.1 Hz, 1H), 4.75-4.69 (m, 1H), 4.27-4.22 (m, 1H), 3.33 (s, 3H), 2.45-2.36 (m, 1H), 2.29-2.15 (m, 2H), 2.10-2.01 (m, 1H), 1.86-1.73 (m, 2H) | 361 |
| 2 | 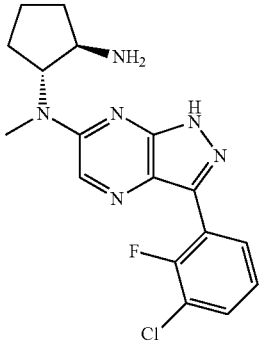<br>single enantiomer, known absolute configuration | $^1$H NMR (400 MHz, CD$_3$OD): δ 8.30 (s, 1H), 7.95-7.99 (m, 1H), 7.50-7.57 (m, 1H), 7.27-7.32 (m, 1H), 4.70-4.90 (m, 1H), 3.25-3.37 (m, 1H), 3.13 (s, 3H), 2.00-2.10 (m, 2H), 1.72-1.92 (m, 3H), 1.44-1.66 (m, 1H) | 360.9 |
| 3 | 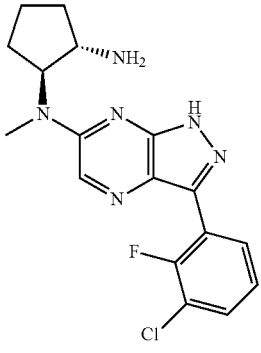<br>single enantiomer, known absolute configuration | $^1$H NMR (400 MHz, DMSO-d6): δ 8.13 (s, 1H), 8.11 (s, 1H), 7.64-7.66 (m, 1H), 7.63 (s, 1H), 4.48-4.51 (m, 1H), 3.21 (s, 1H), 3.03 (s, 3H), 1.90 (m, 2H), 1.88 (m, 3H), 1.86 (m, 1H) | 361.3 |
| 4 | 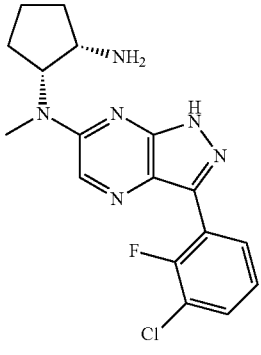<br>single enantiomer, known absolute configuration | $^1$H NMR (400 MHz, CD$_3$OD): δ 8.24 (s, 1H), 8.13-8.10 (m, 1H), 7.46-7.42 (m, 1H), 7.23-7.20 (m, 1H), 4.61-4.55 (m, 1H), 3.92-3.87 (m, 1H), 3.29 (s, 3H), 2.20-2.14 (m, 2H), 2.00-1.95 (m, 2H), 1.67-1.64 (m, 1H), 1.52-1.50 (m, 1H) | 360.9 |

| Example | Structure | Proton NMR | LCMS |
|---|---|---|---|
| 5 | (structure shown) single diastereomer, racemic mixture of enantiomers | $^1$H NMR (400 MHz, CD$_3$OD): δ 8.07 (s, 1H), 8.03-7.99 (m, 1H), 7.62-7.58 (m, 1H), 7.36-7.32 (m, 1H), 4.22-4.17 (m, 1H), 3.23-3.17 (m, 1H), 2.23-2.15 (m, 2H), 1.94-1.65 (m, 2H), 1.91-1.45 (m, 4H) | 361.0 |
| 6 | (structure shown) single enantiomer, known absolute configuration | $^1$H NMR (400 MHz, DMSO-d6): δ 8.24 (br, 3H), 8.10-8.06 (m, 2H), 8.03 (s, 1H), 7.66-7.61 (m, 1H), 7.39-7.34 (m, 1H), 3.96 (m, 1H), 3.14 (m, 1H), 2.16-2.06 (m, 2H), 1.73 (m, 2H), 1.51-1.48 (m, 1H), 1.29 (m, 3H) | 360.9 |
| 7 | (structure shown) single diastereomer, known relative configuration, unknown absolute configuration | $^1$H NMR (400 MHz, DMSO-d6): δ 8.24 (s, 1H), 8.18 (s, 3H), 8.07-8.11 (m, 1H), 7.91 (d, J = 7.2 Hz, 1H), 7.62-7.65 (m, 1H), 7.35-7.40 (m, 1H), 4.28-4.32 (m, 1H), 3.56-3.60 (m, 1H), 1.80-2.00 (m, 2H), 1.60-1.90 (m, 4H), 1.40-1.45 (m, 2H) | 360.9 |
| 8 | (structure shown) single enantiomer, known relative configuration, unknown absolute configuration | $^1$H NMR (400 MHz, CD$_3$OD): δ 8.32 (s, 1H), 8.11-8.05 (m, 2H), 7.61-7.56 (m, 1H), 4.7-4.67 (m, 1H), 4.26-4.21 (m, 1H), 4.15-4.10 (m, 2H), 3.33 (s, 3H), 3.32-3.28 (m, 2H), 2.41-2.28 (m, 4H), 2.27-2.04 (m, 2H), 1.86-1.78 (m, 2H) | 365.0 |

| Example | Structure | Proton NMR | LCMS |
|---|---|---|---|
| 9 | single enantiomer, known absolute configuration | $^1$H NMR (400 MHz, CD$_3$OD): δ 8.37 (s, 2H), 8.21 (s, 1H), 7.87 (d, J = 4.4 Hz, 1H), 7.38 (d, J = 8.4 Hz, 1H), 7.02-6.97 (m, 1H), 4.70-4.62 (m, 1H), 4.24-4.13 (m, 1H), 4.01-3.91 (m, 2H), 3.27 (s, 3H), 3.04 (t, J = 6.4 Hz, 2H), 2.41-2.30 (m, 1H), 2.23-2.08 (m, 4H), 2.05-1.95 (m, 1H), 1.84-1.66 (m, 2H) | 365.0 |
| 10 | single enantiomer, known relative configuration, unknown absolute configuration | $^1$H NMR (400 MHz, CD$_3$OD): δ 8.00-8.10 (m, 3H), 7.55-7.61 (m, 1H), 4.09-4.25 (m, 6H), 3.95-4.02 (m, 1H), 3.27-3.30 (m, 2H), 2.79 (s, 3H), 2.28-2.34 (m, 2H) | 367 |
| 11 | single enantiomer, known relative configuration, unknown absolute configuration | $^1$H NMR (400 MHz, CD$_3$OD): δ 8.05-8.10 (m, 3H), 7.55-7.61 (m, 1H), 4.09-4.25 (m, 6H), 3.95-4.02 (m, 1H), 3.27-3.30 (m, 2H), 2.79 (s, 3H), 2.28-2.34 (m, 2H) | 367 |

-continued

| Example | Structure | Proton NMR | LCMS |
|---|---|---|---|
| 12 | single enantiomer, known absolute configuration | $^1$H NMR (400 MHz, DMSO-d6): δ 13.38 (br d, J = 5.13 Hz, 1H), 9.23 (d, J = 8.30 Hz, 1H), 8.94 (dd, J = 1.71, 4.15 Hz, 1H), 8.36 (dd, J = 0.73, 7.32 Hz, 1H), 8.28 (s, 1H), 8.07 (d, J = 8.30 Hz, 1H), 7.85-7.92 (m, 1H), 7.57 (dd, J = 4.03, 8.67 Hz, 1H), 4.36 (br d, J = 12.45 Hz, 1H), 3.19 (s, 3H), 2.11-2.22 (m, 1H), 1.34-1.85 (m, 8H) | 374.4 |
| 13 | single diastereomer, racemic mixture of enantiomers | $^1$H NMR (400 MHz, DMSO_d$_6$): δ 8.10-8.04 (m, 2H), 7.98-7.89 (m, 4H), 7.66-7.62 (m, 1H), 7.40-7.34 (m, 1H), 3.10-2.96 (m, 1H), 2.64-2.60 (m, 1H), 2.55-2.45 (m, 2H), 2.10-1.96 (m, 2H), 1.78-1.73 (m, 2H), 1.35-1.10 (m, 4H) | 375.0 |
| 14 | single diastereomer, known relative configuration, racemic mixture of enantiomers | $^1$H NMR (400 MHz, DMSO_d$_6$): δ 8.23 (s, 1H), 8.10-8.04 (m, 1H), 7.98-7.89 (m, 3H), 7.76-7.72 (m, 1H), 7.65-7.62 (m, 1H), 7.39-7.34 (m, 1H), 2.78-2.73 (m, 2H), 2.55-2.45 (m, 1H), 2.14-2.12 (m, 1H), 1.80-1.33 (m, 8H) | 374.9 |
| 15 | single enantiomer, known relative configuration, unknown absolute configuration | $^1$H NMR (400 MHz, CD$_3$OD): δ 8.23 (s, 1H), 8.03-7.99 (m, 1H), 7.61-7.56 (m, 1H), 4.45 (br, 1H), 2.92-2.86 (m, 1H), 2.80-2.77 (m, 1H), 2.16-2.13 (m, 1H), 1.98-1.48 (m, 8H). | 374.9 |

| Example | Structure | Proton NMR | LCMS |
|---|---|---|---|
| 16 | 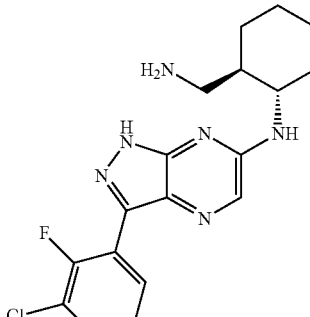<br>single enantiomer, known relative configuration, unknown absolute configuration | $^1$H NMR (400 MHz, CD$_3$OD): δ 7.99-7.92 (m, 2H), 7.58-7.55 (m, 1H), 7.33-7.28 (m, 1H), 3.99-3.88 (m, 1H), 2.85-2.78 (m, 1H), 2.73-2.67 (m, 1H), 2.12-2.10 (m, 1H), 1.95-1.85 (m, 3H), 1.45-1.30 (m, 5H) | 374.9 |
| 17 | 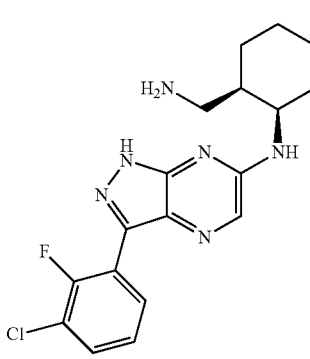<br>single enantiomer, known relative configuration, unknown absolute configuration | $^1$H NMR (400 MHz, CD$_3$OD): δ 8.14 (s, 1H), 7.98-7.93 (m, 1H), 7.56-7.53 (m, 1H), 7.33-7.28 (m, 1H), 4.59 (br, 1H), 2.61-2.56 (m, 2H), 1.92-1.71 (m, 3H), 1.70-1.34 (m, 6H) | 374.9 |
| 18 | 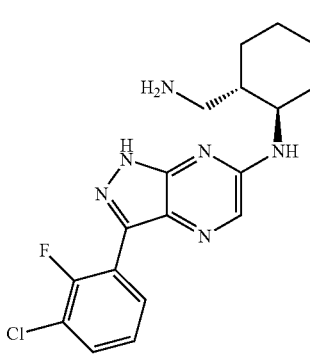<br>single enantiomer, known relative configuration, unknown absolute configuration | $^1$H NMR (400 MHz, CD$_3$OD): δ 8.02-7.97 (m, 2H), 7.58-7.55 (m, 1H), 7.34-7.30 (m, 1H), 3.92-3.86 (m, 1H), 3.16-3.11 (m, 1H), 2.96-2.90 (m, 1H), 2.12-1.78 (m, 5H), 1.52-1.32 (m, 4H) | 374.9 |
| 19 | 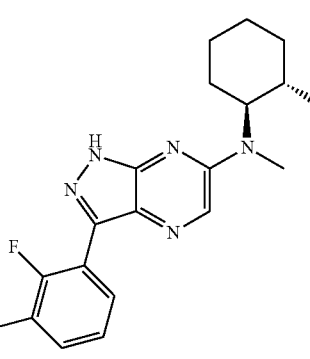<br>single diastereomer, racemic mixture of enantiomers | $^1$H NMR (400 MHz, DMSO-d$_6$): δ 8.38 (s, 1H), 8.13-8.10 (m, 1H), 8.09 (br, 3H), 7.67-7.62 (m, 1H), 7.41-7.36 (m, 1H), 4.65 (br, 1H), 3.32-3.27 (m, 1H), 3.07 (s, 3H), 2.16-2.13 (m, 1H), 1.76-1.68 (m, 4H), 1.54-1.50 (m, 1H), 1.37-1.32 (m, 2H) | 374.9 |

| Example | Structure | Proton NMR | LCMS |
|---|---|---|---|
| 20 | 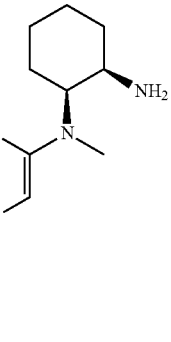<br>single diastereomer, racemic mixture of enantiomers | $^1$H NMR (400 MHz, DMSO_$d_6$): δ 13.51 (s, 1H), 8.36 (s, 1H), 8.21 (s, 3H), 8.11-8.16 (m, 1H), 7.64-7.69 (m, 1H), 7.37-7.41 (m, 1H), 4.53 (d, J = 13.2 Hz, 1H), 3.82 (s, 1H), 3.16 (s, 3H), 2.30-2.34 (m, 1H), 1.99-2.10 (m, 1H), 1.73-1.77 (m, 3H), 1.48-1.52 (m, 3H) | 374.9 |
| 21 | 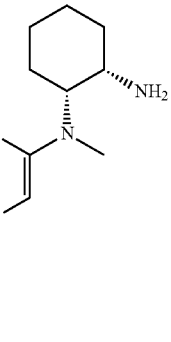<br>single enantiomer, known absolute configuration | $^1$H NMR (400 MHz, DMSO_$d_6$): δ 8.27 (s, 1H), 8.11-8.16 (m, 1H), 7.62-7.67 (m, 1H), 7.35-7.40 (m, 1H), 4.33-4.37 (m, 1H), 3.18 (s, 3H), 1.22-2.30 (m, 9H) | 374.9 |
| 22 | 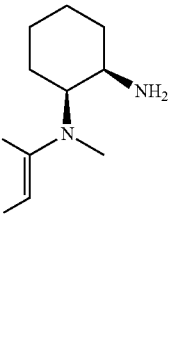<br>single enantiomer, known absolute configuration | $^1$H NMR (400 MHz, DMSO_$d_6$): δ 8.27 (s, 1H), 8.11-8.16 (m, 1H), 7.62-7.67 (m, 1H), 7.35-7.40 (m, 1H), 4.33-4.37 (m, 1H), 3.18 (s, 3H), 1.23-2.30 (m, 9H) | 374.9 |
| 23 | 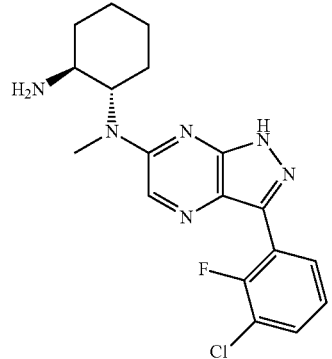<br>single enantiomer, known relative configuration, unknown absolute configuration | $^1$H NMR (400 MHz, CD$_3$OD): δ 8.35 (s, 1H), 8.04-7.99 (m, 1H), 7.62-7.57 (m, 1H), 7.36-7.31 (m, 1H), 4.94 (m, 1H), 3.67-3.59 (m, 1H), 3.20 (s, 3H), 2.29-2.26 (m, 1H), 1.93-1.88 (m, 4H), 1.68-1.62 (m, 1H), 1.53-1.46 (m, 2H) | 375 |

| Example | Structure | Proton NMR | LCMS |
|---|---|---|---|
| 24 | single enantiomer, known relative configuration, unknown absolute configuration | $^1$H NMR (400 MHz, CD$_3$OD): δ 8.36 (s, 1H), 8.05-8.01 (m, 1H), 7.62-7.57 (m, 1H), 7.36-7.31 (m, 1H), 4.94 (m, 1H), 3.67-3.52 (m, 1H), 3.20 (s, 3H), 2.29-2.26 (m, 1H), 1.93-1.88 (m, 4H), 1.68-1.62 (m, 1H), 1.53-1.46 (m, 2H) | 375 |
| 25 | single enantiomer, known absolute configuration | $^1$H NMR (400 MHz, CD$_3$OD): δ 8.27 (s, 1H), 7.96-8.01 (m, 1H), 7.56-7.61 (m, 1H), 7.30-7.35 (m, 1H), 3.66-3.85 (m, 2H), 3.30 (s, 3H), 2.69-2.78 (m, 1H), 2.27-2.35 (m, 1H), 2.00-2.06 (m, 2H), 1.80-1.97 (m, 2H), 1.50-1.70 (m, 2H) | 374.9 |
| 26 | single enantiomer, known relative configuration, unknown absolute configuration | $^1$H NMR (400 MHz, CD$_3$OD): δ 8.29 (s, 1H), 8.01-7.96 (m, 1H), 7.59-7.55 (m, 1H), 7.34-7.29 (m, 1H), 5.15-5.10 (m, 1H), 3.18 (s, 3H), 2.62-2.59 (m, 2H), 2.44 (m, 1H), 2.13-2.00 (m, 4H), 1.76-1.58 (m, 2H) | 375.0 |
| 27 | single enantiomer, known relative configuration, unknown absolute configuration | $^1$H NMR (400 MHz, CD$_3$OD): δ 8.28 (s, 1H), 7.80-7.96 (m, 1H), 7.60-7.55 (m, 1H), 7.34-7.29 (m, 1H), 3.15 (s, 3H), 2.81-2.69 (m, 1H), 2.68-2.64 (m, 1H), 2.06-1.98 (m, 1H), 1.86-1.85 (m, 2H), 1.83-1.82 (m, 3H), 1.53-1.49 (m, 2H) | 375.0 |

| Example | Structure | Proton NMR | LCMS |
|---|---|---|---|
| 28 | 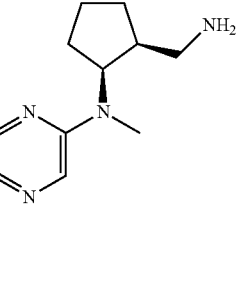<br>single enantiomer, known relative configuration, unknown absolute configuration | ¹H NMR (400 MHz, CD₃OD): δ 8.29 (s, 1H), 8.01-7.96 (m, 1H), 7.59-7.55 (m, 1H), 7.34-7.29 (m, 1H), 5.15-5.10 (m, 1H), 3.18 (s, 3H), 2.62-2.59 (m 2H), 2.44 (m, 1H), 2.13-2.00 (m, 4H), 1.76-1.58 (m, 2H) | 375.0 |
| 29 | 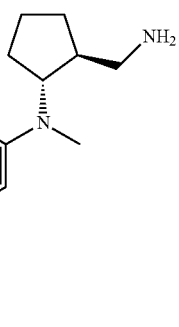<br>single enantiomer, known relative configuration, unknown absolute configuration | ¹H NMR (400 MHz, CD₃OD): δ 8.28 (s, 1H), 7.80-7.96 (m, 1H), 7.60-7.55 (m, 1H), 7.34-7.29 (m, 1H), 3.15 (s, 3H), 2.81-2.69 (m, 1H), 2.68-2.64 (m, 1H), 2.06-1.98 (m, 1H), 1.86-1.85 (m, 2H), 1.83-1.82 (m, 3H), 1.53-1.49 (m, 2H) | 375.0 |
| 30 | 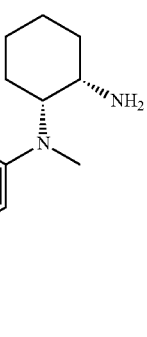<br>single enantiomer, known absolute configuration | ¹H NMR (400 MHz, DMSO-d₆): δ 8.29-8.41 (m, 3H), 4.36 (br d, J = 12.21 Hz, 2H), 3.18 (s, 3H), 2.08-2.27 (m, 2H), 1.81 (br d, J = 12.21 Hz, 2H), 1.58-1.69 (m, 2H), 1.47-1.57 (m, 2H), 1.39 (br d, J = 10.74 Hz, 2H), 1.22 (br s, 1H) | 376.0 |
| 31 | 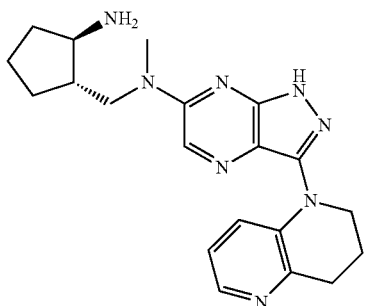<br>single enantiomer, known relative configuration, unknown absolute configuration | ¹H NMR (400 MHz, CD₃OD): δ 8.22 (s, 1H), 8.07-8.05 (m, 2H), 7.60-7.57 (m, 1H), 4.12-4.08 (m, 2H), 3.93-3.87 (m, 1H), 3.79-3.75 (m, 1H), 3.50-3.42 (m, 1H), 3.32-3.30 (m, 5H), 2.55-2.45 (m, 1H), 2.35-2.23 (m, 4H), 2.10-2.00 (m, 1H), 1.77-1.74 (m, 1H) | 379.1 |

| Example | Structure | Proton NMR | LCMS |
|---|---|---|---|
| 32 | 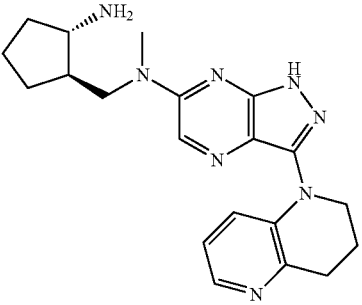<br>single enantiomer, known relative configuration, unknown absolute configuration | ¹H NMR (400 MHz, CD₃OD): δ 8.22 (s, 1H), 8.07-8.05 (m, 2H), 7.60-7.55 (m, 1H), 4.12-4.08 (m, 2H), 3.93-3.87 (m, 1H), 3.80-3.74 (m, 1H), 3.50-3.42 (m, 1H), 3.29-3.26 (m, 5H), 2.54-2.45 (m, 1H), 2.33-2.23 (m, 4H), 2.05-1.95 (m, 1H), 1.77-1.74 (m, 1H) | 379 |
| 33 | 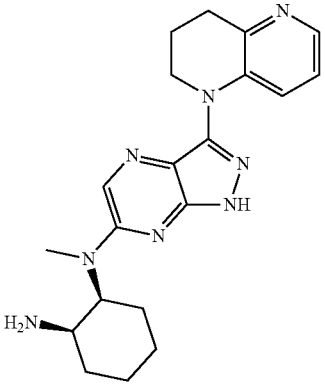<br>single enantiomer, known absolute configuration | ¹H NMR (400 MHz, CD₃OD): δ 8.25 (s, 1H), 8.11-8.06 (m, 2H), 7.60-7.56 (m, 1H), 4.77-4.72 (m, 1H), 4.14-4.09 (m, 3H), 3.33-3.27 (m, 2H), 3.26 (s, 3H), 2.34-2.30 (m, 2H), 2.18-2.07 (m, 1H), 2.02-1.95 (m, 4H), 1.61-1.52 (m, 3H) | 379.0 |
| 34 | 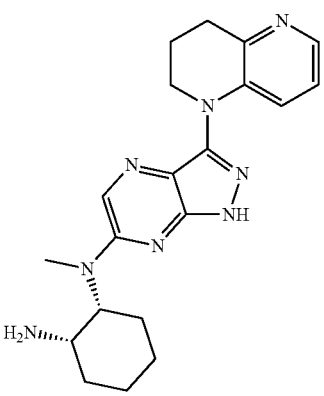<br>single enantiomer, known relative configuration, unknown absolute configuration | ¹H NMR (400 MHz, CD₃OD): δ 8.23 (s, 1H), 8.10-8.00 (m, 2H), 7.59-7.54 (m, 1H), 4.74-4.69 (m, 1H), 4.21-4.08 (m, 3H), 3.29-3.26 (m, 2H), 3.24 (s, 3H), 2.40-2.26 (m, 2H), 2.25-2.13 (m, 1H), 2.12-1.82 (m, 4H), 1.74-1.70 (m, 1H), 1.69-1.44 (m, 2H) | 379.1 |

-continued

| Example | Structure | Proton NMR | LCMS |
|---|---|---|---|
| 35 | single enantiomer, known absolute configuration | ¹H NMR (400 MHz, CD₃OD): δ 8.18 (s, 1H), 7.88 (d, J = 4.8 Hz, 1H), 7.33 (d, J = 8.4 Hz, 1H), 6.98-7.03 (m, 1H), 4.19-4.24 (m, 1H), 4.03-4.09 (m, 1H), 3.94-3.98 (m, 2H), 3.87-3.92 (m, 1H), 3.64-3.71 (m, 1H), 3.49-3.54 (m, 1H), 3.46 (s, 3H), 3.04-3.08 (m, 2H), 2.18-2.25 (m, 2H), 1.80-1.86 (m, 2H) | 381.0 |
| 36 | single enantiomer, known absolute configuration | ¹H NMR (400 MHz, CD₃OD): δ 8.29 (s, 1H), 8.12-8.06 (m, 2H), 7.61-7.57 (m, 1H), 4.97 (m, 2H), 4.24-4.20 (m, 1H), 4.16-4.11 (m, 3H), 4.05 (s, 1H), 3.92-3.88 (m, 1H), 3.75-3.68 (m, 1H), 3.30 (s, 1H), 3.29 (s, 3H), 2.63-2.58 (m, 1H), 2.36-2.30 (m, 2H), 1.92-1.87 (m, 1H) | 381.0 |
| 37 | single enantiomer, known absolute configuration | ¹H NMR (400 MHz, CD₃OD): δ 8.15 (s, 1H), 7.89-7.87 (d, J = 4.0 Hz, 1H), 7.34-7.32 (d, J = 7.6 Hz, 1H), 7.03-6.98 (m, 1H), 4.78-4.77 (m, 2H), 4.11 (m, 1H), 3.98-3.89 (m, 3H), 3.79-3.75 (m, 1H), 3.62 (m, 1H), 3.28 (s, 3H), 3.08-3.04 (m, 2H), 2.5 (m, 1H), 2.23-2.18 (m, 2H), 2.02-2.03 (m, 1H) | 380.9 |

| Example | Structure | Proton NMR | LCMS |
|---|---|---|---|
| 38 | 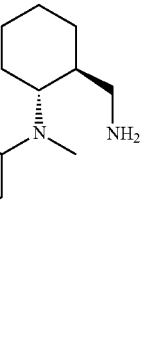 single enantiomer, known absolute configuration | | 389.0 |
| 39 | 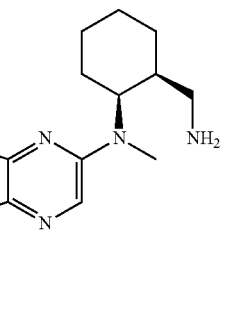 single enantiomer, known absolute configuration | $^1$H NMR (400 MHz, CD$_3$OD): δ 8.31 (s, 1H), 7.99-8.03 (m, 1H), 7.56-7.61 (m, 1H), 7.30-7.35 (m, 1H), 4.60-4.64 (m, 1H), 3.16 (s, 3H), 2.96-2.30 (m, 1H), 2.73-2.80 (m, 1H), 2.03-2.11 (m, 2H), 1.83-1.97 (m, 4H), 1.36-1.52 (m, 3H) | 389.0 |
| 40 | 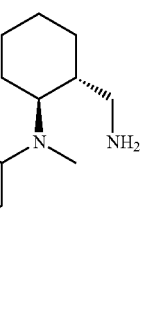 single enantiomer, known absolute configuration | $^1$H NMR (400 MHz, CD$_3$OD): δ 8.26 (s, 1H), 7.95-7.97 (m, 1H), 7.53-7.57 (m, 1H), 7.27-7.32 (m, 1H), 4.60-4.68 (m, 1H), 3.21 (s, 3H), 2.90-2.94 (m, 1H), 2.65-2.70 (m, 1H), 1.80-2.10 (m, 3H), 1.77-1.79 (m, 2H), 1.48-1.68 (m, 4H) | 389.0 |
| 41 | 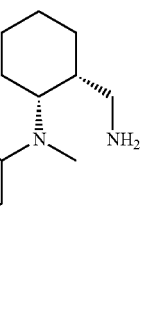 single enantiomer, known absolute configuration | $^1$H NMR (400 MHz, CD$_3$OD): δ 8.31 (s, 1H), 7.99-8.03 (m, 1H), 7.56-7.61 (m, 1H), 7.30-7.35 (m, 1H), 4.60-4.65 (m, 1H), 3.16 (s, 3H), 2.96-2.99 (m, 1H), 2.73-2.79 (m, 1H), 2.03-2.11 (m, 2H), 1.83-1.96 (m, 4H), 1.36-1.53 (m, 3H) | 389.0 |

-continued

| Example | Structure | Proton NMR | LCMS |
|---|---|---|---|
| 42 | 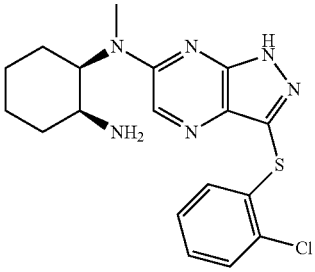 single enantiomer, known absolute configuration | $^1$H NMR (400 MHz, DMSO-d$_6$): δ 8.16-8.33 (m, 1H), 7.33-7.59 (m, 1H), 7.23-7.03 (m, 2H), 6.74 (dd, J = 7.69, 1.59 Hz, 1H), 4.24-4.45 (m, 1H), 3.14 (s, 3H), 2.01-2.23 (m, 1H), 1.80 (br d, J = 12.45 Hz, 2H), 1.64 (br s, 2H), 1.47-1.56 (m, 2H), 1.29-1.45 (m, 2H) | 389.3 |
| 43 | 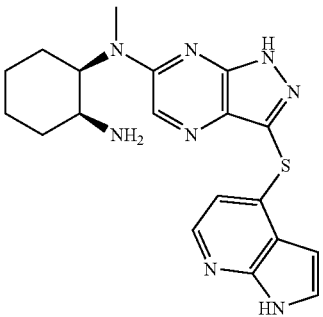 single enantiomer, known absolute configuration | $^1$H NMR (400 MHz, DMSO-d$_6$): δ 11.75 (br s, 1H), 8.30 (s, 1H), 8.18 (s, 1H), 7.93 (d, J = 5.03 Hz, 1H), 7.33-7.55 (m, 1H), 6.49 (d, J = 5.03 Hz, 1H), 6.27-6.39 (m, 1H), 4.34 (br d, J = 12.51 Hz, 1H), 3.14 (s, 3H), 2.00-2.25 (m, 1H), 1.72-1.85 (m, 2H), 1.65 (br dd, J = 5.80, 3.20 Hz, 2H), 1.45-1.58 (m, 2H), 1.30-1.45 (m, 2H) | 395.5 |
| 44 | 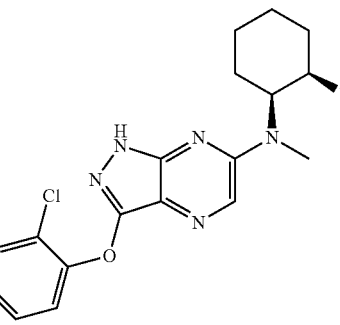 single enantiomer, known absolute configuration | $^1$H NMR (400 MHz, DMSO-d$_6$): δ 13.00 (br, 1H), 8 26-8 24 (m, 2H), 8.22 (br, 3H), 7.15-7.12 (d, J = 6.0 Hz, 1H), 4.52-4.48 (m, 1H), 3.78 (m, 1H), 3.13 (s, 3H), 2.33 (m, 1H), 2.06-2.02 (m, 1H), 1.88-1.69 (m, 3H), 1.55-1.45 (m, 3H) | 407.9 |
| 45 | 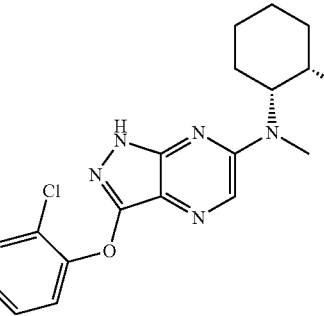 single enantiomer, known absolute configuration | $^1$H NMR (400 MHz, DMSO-d$_6$): δ 13.00 (s, 1H), 8.24-8.29 (m, 2H), 8.10 (br, 3H), 7.14 (d, J = 5.6 Hz, 1H), 4.48-4.53 (m, 1H), 3.77-3.80 (m, 1H), 3.12 (s, 3H), 2.22-2.27 (m, 1H), 1.97-2.03 (m, 1H), 1.80-1.95 (m, 1H), 1.65-1.85 (m, 2H), 1.40-1.63 (m, 3H) | 407.9 |

| Example | Structure | Proton NMR | LCMS |
|---|---|---|---|
| 46 | 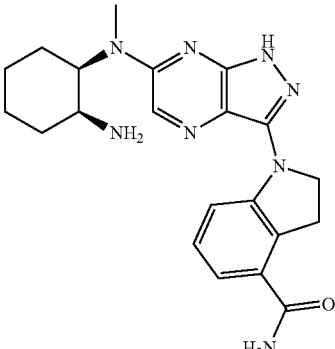<br>single enantiomer, known absolute configuration | ¹H NMR (400 MHz, DMSO-d$_6$): δ 12.33 (s, 1H), 8.11-8.21 (m, 1H), 8.00-8.11 (m, 1H), 7.72 (br s, 1H), 7.28 (br s, 1H), 7.13-7.21 (m, 1H), 7.07-7.13 (m, 1H), 4.35-4.54 (m, 4H), 3.45 (br t, J = 8.67 Hz, 2H), 3.10 (s, 3H), 2.05-2.21 (m, 2H), 1.62-1.95 (m, 4H), 1.33-1.57 (m, 2H) | 407.5 |

SHP2 Allosteric Inhibition Assay.

SHP2 is allosterically activated through binding of bis-tyrosyl-phorphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

More specifically, the phosphatase reactions were performed at room temperature in 96-well black polystyrene plate, flat bottom, low flange, non-binding surface (Corning, Cat #3575) using a final reaction volume of 50 µl and the following assay buffer conditions: 60 mM HEPES, pH 7.2, 75 mM NaCl, 75 mM KCl, 1 mM EDTA 0.005% Brij-35, 5 mM DTT.

The inhibition of SHP2 by compounds of the disclosure (concentrations varying from 0.003-100 µM) was monitored using an assay in which 0.25 nM of SHP2 was incubated with of 0.5 µM of peptide IRS1_pY1172(dPEG8)pY1222 (sequence: H2N-LN(pY)IDLDLV(dPEG8)LST(pY)AS-INFQK-amide). After 30-60 minutes incubation at 25° C. the surrogate substrate DiFMUP (Invitrogen, cat #D6567, 100 µM final) was added to the reaction and the conversion of DiFMUP to 6,8-difluoro-7-hydroxy-4-methylcoumarin (DiFMU) was monitored continuously for 10 minutes with excitation at 355 nm and emission at 460 nm using a microplate reader (PolarStar, BMG). The inhibitor dose response curves were analyzed using normalized IC$_{50}$ regression curve fitting with control based normalization.

Biochemical assay results for compounds of the disclosure are shown in examples and Table 1. In Table 1, A means an IC$_{50}$ of less than 1 µM: B means an IC$_{50}$ equal to 1 µM but less than 10 µM; and C means an IC$_{50}$ of 10 µM or more.

TABLE 1

| SHP2 IC$_{50}$ Assay Results | |
|---|---|
| Example | SHP2 IC$_{50}$ |
| 1 | B |
| 2 | A |
| 3 | A |
| 4 | A |
| 5 | B |

TABLE 1-continued

| SHP2 IC$_{50}$ Assay Results | |
|---|---|
| Example | SHP2 IC$_{50}$ |
| 6 | B |
| 7 | B |
| 8 | B |
| 9 | C |
| 10 | C |
| 11 | C |
| 12 | A |
| 13 | A |
| 14 | A |
| 15 | A |
| 16 | A |
| 17 | B |
| 18 | B |
| 19 | A |
| 20 | A |
| 21 | A |
| 22 | A |
| 23 | B |
| 24 | A |
| 25 | A |
| 26 | A |
| 27 | A |
| 28 | A |
| 29 | A |
| 30 | A |
| 31 | C |
| 32 | C |
| 33 | C |
| 34 | B |
| 35 | C |
| 36 | B |
| 37 | C |
| 38 | A |
| 39 | A |
| 40 | A |
| 41 | A |
| 42 | A |
| 43 | A |
| 44 | B |
| 45 | A |
| 46 | A |

INCORPORATION BY REFERENCE

Certain subject matter disclosed herein was made pursuant to a joint research agreement between Relay Therapeutics, Inc. and D.E. Shaw Research, LLC. All patents, patent applications and publications cited herein are hereby incorporated by reference in their entirety. The disclosures of these publications in their entireties are hereby incorporated by reference into this application in order to more fully describe the state of the art as known to those skilled therein as of the date of the disclosure described and claimed herein.

Although the disclosure has been described and illustrated in the foregoing illustrative embodiments, it is understood that the present disclosure has been made only by way of example, and that numerous changes in the details of implementation of the disclosure can be made without departing from the spirit and scope of the disclosure, which is limited only by the claims that follow. Features of the disclosed embodiments can be combined and rearranged in various ways within the scope and spirit of the disclosure.

What is claimed is:
1. A compound of Formula (I):

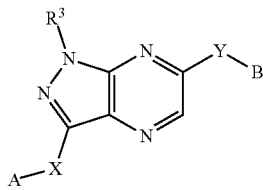

(I)

or a pharmaceutically acceptable salt or stereoisomer thereof,
wherein:
A is a 4-7 membered heterocyclyl, a monocyclic or bicyclic 6-10 membered aryl, a monocyclic 5-7 membered heteroaryl, or a bicyclic 8-10 membered heteroaryl, wherein the monocyclic 5-7 membered heteroaryl or the bicyclic 8-10 membered heteroaryl has 1 or more heteroatoms independently selected from the group consisting of N, O, and S, and further wherein A is optionally substituted by one or more substituents independently selected from the group consisting of halogen, cyano, $C(O)R^{10}$, $C(O)N(R^{10})_2$, $N(R^{10})_2$, $NR^{10}C(O)R^{10}$, $NR^{10}S(O)_wR^{10}$, $OR^{10}$, $=O$, $OS(O)_w R^{10}$, $P(O)(R^{10})_2$, $S(O)_w R^{10}$, $S(O)_w N(R^{10})_2$, and $R^{10}$;
X is a bond, $-CR^{X2}R^{X3}-$, $-CR^{X4}R^{X5}NR^{X1}-$, $-CR^{X4}R^{X5}O-$, $-CR^{X6}=CR^{X7}-$, $-C\equiv C-$, $-C(O)-$, $-C(O)NR^{X11}-$, $-NR^{X1}-$, $-NR^{X1}CR^{X4}R^{X5}$, $-O-$, $-OCR^{X4}R^{X5}-$, $-S(O)_w-$, or cyclopropyl;
$R^{X1}$ is H, $C_{1-6}$ alkyl, or phenyl; or
$R^{X1}$ and A, together with the nitrogen atom to which they are attached, form a saturated or partially unsaturated 8-10 membered bicyclic heterocyclyl, wherein the saturated or partially unsaturated 8-10 membered bicyclic heterocyclyl optionally has 1 or more additional heteroatoms independently selected from the group consisting of N, O, and S, and further wherein the saturated or partially unsaturated 8-10 membered bicyclic heterocyclyl is optionally substituted by one or more substituents independently selected from the group consisting of halogen, cyano, $C(O)R^{10}$, $C(O)N(R^{10})_2$, $N(R^{10})_2$, $OR^{10}$, $=O$, $OS(O)_wR^{10}$, $P(O)(R^{10})$, $S(O)_w R^{10}$, $S(O)_w N(R^{10})_2$, and $R^{10}$;
$R^{X2}$ is H, halogen, $C_{1-6}$ alkyl, $C(O)NR^aR^b$, $N^aR^b$, OH, or $OC_{1-6}$ alkyl, wherein the $C_{1-6}$ alkyl or $OC_{1-6}$ alkyl is optionally substituted by one or more independently selected $R^P$ substituents;

$R^{X3}$ is H, halogen, $C_{1-6}$ alkyl, $C(O)NR^aR^b$, $N^aR^b$, OH, or $OC_{1-6}$ alkyl, wherein the $C_{1-6}$ alkyl or $OC_{1-6}$ alkyl is optionally substituted by one or more independently selected $R^P$ substituents; or
$R^{X2}$ and $R^{X3}$, together with the carbon atom to which they are attached, form a 3-6 membered carbocyclyl, wherein the 3-6 membered carbocyclyl is optionally substituted by one or more substituents independently selected from the group consisting of halogen, $C_{1-6}$ alkyl, $C(O)NR^aR^b$, $NR^aR^b$, $OC_{1-6}$ alkyl, and $=O$;
$R^{X4}$ is H or $C_{1-6}$ alkyl, wherein the $C_{1-6}$ alkyl is optionally substituted by one or more independently selected $R^P$ substituents;
$R^{X5}$ is H or $C_{1-6}$ alkyl, wherein the $C_{1-6}$ alkyl is optionally substituted by one or more independently selected $R^P$ substituents;
$R^{X6}$ is H, halogen, CN, $C_{1-6}$ alkyl, or $C(O)NR^aR^b$, wherein the $C_{1-6}$ alkyl is optionally substituted by one or more independently selected $R^P$ substituents;
$R^{X7}$ is H, halogen, CN, $C_{1-6}$ alkyl, or $C(O)NR^aR^b$, wherein the $C_{1-6}$ alkyl is optionally substituted by one or more independently selected $R^P$ substituents;
$R^{X11}$ is H, $C_{1-6}$ alkyl, or phenyl; or
$R^{X11}$ and A, together with the nitrogen atom to which they are attached, form a saturated or partially unsaturated 8-10 membered bicyclic heterocyclyl, wherein the saturated or partially unsaturated 8-10 membered bicyclic heterocyclyl optionally has 1 or more additional heteroatoms independently selected from the group consisting of N, O, and S, and further wherein the saturated or partially unsaturated 8-10 membered bicyclic heterocyclyl is optionally substituted by one or more substituents independently selected from the group consisting of halogen, cyano, $C(O)R^{10}$, $C(O)N(R^{10})_2$, $N(R^{10})_2$, $OR^{10}$, $=O$, $OS(O)_w R^{10}$, $P(O)(R^{10})_2$, $S(O)_w R^{10}$, $S(O)_w N(R^{10})_2$, $S(O)NHR^{10}$, and $R^{10}$;
each $R^{10}$ is independently H, $C_{1-6}$ alkyl, $C_{2-6}$ heteroalkyl, $C_{3-6}$ cycloalkyl, heterocycloalkyl, aryl, or heteroaryl, wherein each $C_{1-6}$ alkyl, $C_{2-6}$ heteroalkyl, $C_{3-6}$ cycloalkyl, heterocycloalkyl, aryl, and heteroaryl is optionally and independently substituted by one or more substituents independently selected from the group consisting of halogen, $C_{1-6}$ alkyl, $C_{1-6}$ haloalkyl, $C(NR^a)R^b$, $C(O)R^{20}$, $N^aR^b$, OH, and $OC_{1-6}$ alkyl;
each $R^{20}$ is independently H, halogen, $C_{1-6}$ alkyl, $NR^aR^b$, OH, or $OC_{1-6}$ alkyl;
Y is $-C_{1-3}$ alkylene-$NR^Y-$, $-NR^Y-$, or $-NR^Y-C_{1-3}$ alkylene-;
$R^Y$ is H, $C_{1-6}$ alkyl, or phenyl;
B is a saturated 3-7 membered carbocyclyl or a saturated 4-7 membered heterocyclyl, wherein the saturated 4-7 membered heterocyclyl has 1 or 2 heteroatoms or heteroatomic groups independently selected from the group consisting of $NR^b$, O, and $S(O)_w$, and further wherein the saturated 3-7 membered carbocyclyl or the saturated 4-7 membered heterocyclyl is optionally substituted on one or more available carbons by one or more substituents independently selected from the group consisting of halogen, cyano, $C_{1-6}$ alkyl, $C_{2-6}$ alkenyl, $C_{2-6}$ alkynyl, $C(O)C_{1-6}$ alkyl, $C(O)NR^aR^b$, C(O)OH, $C(O)OC_{1-6}$ alkyl, $NR^aR^b$, $NR^aC(O)C_{1-6}$ alkyl, $NR^aC(O)OC_{1-6}$ alkyl, $NR^aS(O)_2C_{1-6}$ alkyl, OH, $OC_{1-6}$ alkyl, $OC_{3-6}$ alkenyl, $OC_{3-6}$ alkynyl, $=O$, $S(O)_w C_{1-6}$ alkyl, $S(O)_2NR^aR^b$, $C_{3-6}$ cycloalkyl, $C_{3-6}$ cycloalkoxy, aryl, and heteroaryl, wherein each $C_{1-6}$ alkyl, $C_{2-6}$ alkenyl, $C_{2-6}$ alkynyl, $C(O)C_{1-6}$ alkyl, $C(O)OC_{1-6}$ alkyl, $NR^aC(O)C_{1-6}$ alkyl, $NR^aC(O)OC_{1-6}$ alkyl, NR$^a$S(O)$_2$C$_{1-6}$ alkyl, OC$_{1-6}$ alkyl, OC$_{3-6}$ alkenyl, OC$_{3-6}$ alkynyl, S(O)C$_{1-6}$ alkyl, C$_{3-6}$ cycloalkyl, and C$_{3-6}$ cycloalkoxy is optionally and independently substituted by one or more independently selected R$^P$ substituents, and further wherein each aryl and heteroaryl is optionally and independently substituted by one or more independently selected R$^f$ substituents;

each R$^f$ is independently R$^P$, C$_{1-6}$ alkyl, C$_{2-6}$ alkenyl, C$_{2-6}$ alkynyl, C(O)C$_{1-6}$ alkyl, C(O)OC$_{1-6}$ alkyl, NR$^a$C(O)C$_{1-6}$ alkyl, NR$^a$C(O)OC$_{1-6}$ alkyl, OC$_{1-6}$ alkyl, S(O)$_w$C$_{1-6}$ alkyl, or C$_{3-6}$ cycloalkyl, wherein each C$_{1-6}$ alkyl, C$_{2-6}$ alkenyl, C$_{2-6}$ alkynyl, C(O)C$_{1-6}$ alkyl, C(O)OC$_{1-6}$ alkyl, NR$^a$C(O)C$_{1-6}$ alkyl, NR$^a$C(O)OC$_{1-6}$ alkyl, OC$_{1-6}$ alkyl, S(O)$_w$C$_{1-6}$ alkyl, and C$_{3-6}$ cycloalkyl is optionally and independently substituted by one or more independently selected R$^P$ substituents;

each R$^h$ is independently H, C$_{1-6}$ alkyl, C$_{3-6}$ alkenyl, C$_{3-6}$ alkynyl, C(O)C$_{1-6}$ alkyl, C(O)NR$^a$R$^b$, C(O)OC$_{1-6}$ alkyl, S(O)$_2$C$_{1-6}$ alkyl, S(O)$_2$NR$^a$R$^b$, or C$_{3-6}$ cycloalkyl, wherein each C$_{1-6}$ alkyl, C$_{3-6}$ alkenyl, C$_{3-6}$ alkynyl, C(O)C$_{1-6}$ alkyl, C(O)OC$_{1-6}$ alkyl, S(O)$_2$C$_{1-6}$ alkyl, and C$_{3-6}$ cycloalkyl is optionally and independently substituted by one or more independently selected R$^P$ substituents;

each R$^P$ is independently halogen, cyano, C(O)NR$^a$R$^b$, N$^a$R$^b$, NR$^a$C(O)NR$^a$R$^b$, OH, OC$_{1-6}$ alkyl, or SO$_2$NR$^a$R$^b$;

R$^a$ is H or C$_{1-6}$ alkyl, wherein the C$_{1-6}$ alkyl is optionally substituted by one or more substituents independently selected from the group consisting of halogen, cyano, OH, and =O;

R$^b$ is H or C$_{1-6}$ alkyl, wherein the C$_{1-6}$ alkyl is optionally substituted by one or more substituents independently selected from the group consisting of halogen, cyano, OH, and =O; or R$^a$ and R$^b$, together with the nitrogen atom to which they are attached, form a monocyclic 4-6 membered heterocyclyl, wherein the monocyclic 4-6 membered heterocyclyl optionally has an additional heteroatom selected from the group consisting of N, O, and S, and further wherein the monocyclic 4-6 membered heterocyclyl is optionally substituted by one or more substituents independently selected from the group consisting of halogen, cyano, OH, and =O;

R$^3$ is H, C$_{1-6}$ alkyl, or phenyl; and each w is independently 0, 1, or 2.

2. The compound of claim 1, or a pharmaceutically acceptable salt or stereoisomer thereof, wherein A is phenyl, pyridyl, indolinyl, indolyl, or quinolinyl, wherein the phenyl, pyridyl, indolinyl, indolyl, or quinolinyl is optionally substituted by one, two or three substituents independently selected from the group consisting of halogen, cyano, C(O)N(R$^{10}$)$_2$, N(R$^{10}$)$_2$, OR$^{10}$, OS(O)$_2$R$^{10}$, SR$^{10}$, S(O)$_2$R$^{10}$, and R$^{10}$.

3. The compound of claim 1, or a pharmaceutically acceptable salt or stereoisomer thereof, wherein A is phenyl; wherein the phenyl is optionally substituted by one, two, or three substituents independently selected from the group consisting of halogen, cyano, and OR$^{10}$.

4. The compound of claim 1, or a pharmaceutically acceptable salt or stereoisomer thereof, wherein A is pyridyl; wherein the pyridyl is optionally substituted by one, two, or three substituents independently selected from the group consisting of halogen, cyano, and OR$^{10}$.

5. The compound of claim 1, or a pharmaceutically acceptable salt or stereoisomer thereof, wherein X is a bond, —O—, —S—, or —NR$^{X1}$—.

6. The compound of claim 1, or a pharmaceutically acceptable salt or stereoisomer thereof, wherein R$^{X1}$ and ring A, together with the nitrogen atom to which they are attached, form 1,2,3,4-tetrahydro-1,5napthyridinyl.

7. The compound of claim 1, or a pharmaceutically acceptable salt or stereoisomer thereof, wherein Y is —CH$_2$NR$^Y$—, —NR$^Y$—, or —NR$^Y$CH$_2$—.

8. The compound of claim 1, or a pharmaceutically acceptable salt or stereoisomer thereof, wherein Y is —NH—, —N(CH$_3$)—, —NHCH$_2$—, or —N(CH$_3$)CH$_2$—.

9. The compound of claim 1, or a pharmaceutically acceptable salt or stereoisomer thereof, wherein:

B is cyclopentyl, wherein the cyclopentyl is optionally substituted by one, two, r three substituents independently selected from the group consisting of halogen, cyano, C$_{1-3}$ alkyl, C(O)NR$^a$R$^b$, N$^a$R$^b$, OH, and OC$_{1-3}$ alkyl, wherein each C$_{1-3}$ alkyl and OC$_{1-3}$ alkyl is optionally and independently substituted by one, two, or three independently selected R$^P$ substituents; and each R$^P$ is independently halogen, NR$^a$R$^b$, or OH.

10. The compound of claim 1, or a pharmaceutically acceptable salt or stereoisomer thereof, wherein:

B is cyclohexyl, wherein the cyclohexyl is optionally substituted by one, two, r three substituents independently selected from the group consisting of halogen, cyano, C$_{1-3}$ alkyl, C(O)NR$^a$R$^b$, N$^a$R$^b$, OH, and OC$_{1-3}$ alkyl, wherein each C$_{1-3}$ alkyl and OC$_{1-3}$ alkyl is optionally and independently substituted by one, two, or three independently selected R$^P$ substituents; and each R$^P$ is independently halogen, NR$^a$R$^b$, or OH.

11. The compound of claim 1, or a pharmaceutically acceptable salt or stereoisomer thereof, wherein:

B is tetrahydrofuranyl, wherein the tetrahydrofuranyl is optionally substituted by one, two, g three substituents independently selected from the group consisting of halogen, cyano, C$_{1-3}$ alkyl, C(O)NR$^a$R$^b$, N$^a$R$^b$, OH, and OC$_{1-3}$ alkyl, wherein each C$_{1-3}$ alkyl and OC$_{1-3}$ alkyl is optionally and independently substituted by one, two, or three independently selected R$^P$ substituents; and each R$^P$ is independently halogen, NR$^a$R$^b$, or OH.

12. The compound of claim 1, or a pharmaceutically acceptable salt or stereoisomer thereof, wherein:

B is tetrahydropyranyl, wherein the tetrahydropyranyl is optionally substituted by one, two, or three substituents independently selected from the group consisting of halogen, cyano, C$_{1-3}$ alkyl, C(O)NR$^a$R$^b$, N$^a$R$^b$, OH, and OC$_{1-3}$ alkyl, wherein each C$_{1-3}$ alkyl and OC$_{1-3}$ alkyl is optionally and independently substituted by one, two, or three independently selected R$^P$ substituents; and each R$^P$ is independently halogen, NR$^a$R$^b$, or OH.

13. The compound of claim 1, or a pharmaceutically acceptable salt or stereoisomer thereof, wherein ring B is substituted on an available carbon by one substituent selected from the group consisting of CH$_2$NH$_2$ and NH$_2$.

14. The compound of claim 1, or a pharmaceutically acceptable salt or stereoisomer thereof, wherein B is:

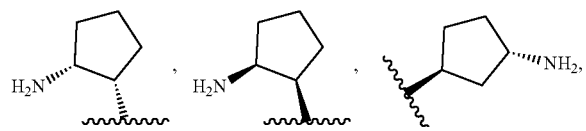

75

-continued

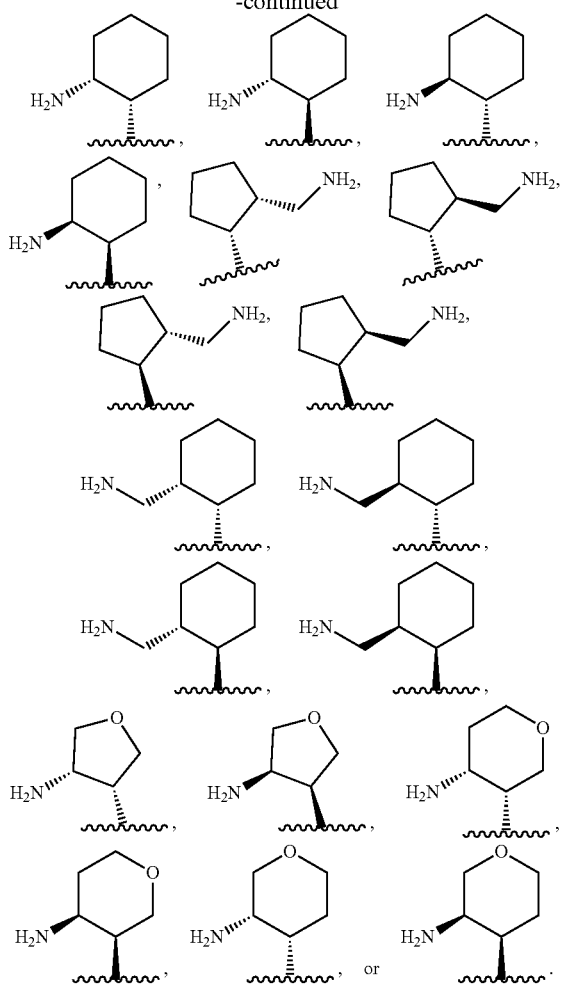

15. The compound of claim 1, wherein the compound is of Formula (II):

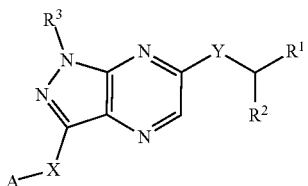

or a pharmaceutically acceptable salt or stereoisomer thereof,
wherein:
$R^1$ and $R^2$, together with the carbon atom to which they are attached, form a saturated 3-7 membered carbocyclyl or a saturated 4-7 membered heterocyclyl, wherein the saturated 4-7 membered heterocyclyl has 1 or 2 heteroatoms or heteroatomic groups independently selected from the group consisting of $NR^h$, O, and $S(O)_w$.

16. The compound of claim 1, or a pharmaceutically acceptable salt or stereoisomer thereof, wherein $R^3$ is H or $CH_3$.

76

17. A pharmaceutical composition comprising a pharmaceutically acceptable carrier and a compound of claim 1, or a pharmaceutically acceptable salt or stereoisomer thereof.

18. A method for inhibiting Src homology region 2-containing protein tyrosine phosphatase 2 activity in a subject in need thereof, comprising administering to the subject a therapeutically effective amount of a compound of claim 1, or a pharmaceutically acceptable salt or stereoisomer thereof.

19. The method of claim 18, wherein the subject has a disorder selected from the group consisting of acute myeloid leukemia, breast cancer, colorectal cancer, diabetes, juvenile leukemia, lung cancer, melanoma, myelomonocytic leukemia, neuroblastoma, neutropenia, and Noonan syndrome.

20. The method of claim 18, wherein the method further comprises administering to the subject a therapeutically effective amount of an antibody, an antibody-drug conjugate, an immunomodulator, or a histone deacetylase inhibitor.

21. A compound of Formula (III):

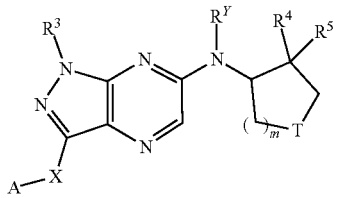

wherein:
A is a 4-7 membered heterocyclyl, phenyl, or a monocyclic 5-7 membered heteroaryl, wherein the monocyclic 5-7 membered heteroaryl has 1 or more heteroatoms independently selected from the group consisting of N, O, and S, and further wherein A is optionally substituted by one or more substituents independently selected from the group consisting of halogen, cyano, $C(O)N(R^{10})_2$, $N(R^{10})_2$, $OR^{10}$, =O, and $R^{10}$;

X is a bond, $-CR^{X2}R^{X3}-$, $-C(O)-$, $-NR^{X1}-$, $-O-$, or $-S(O)_w-$;

$R^{X1}$ is H, $C_{1-6}$ alkyl, or phenyl; or $R^{X1}$ and A, together with the nitrogen atom to which they are attached, form a saturated or partially unsaturated 8-10 membered bicyclic heterocyclyl, wherein the saturated or partially unsaturated 8-10 membered bicyclic heterocyclyl optionally has 1 or more additional heteroatoms independently selected from the group consisting of N, O, and S, and further wherein the saturated or partially unsaturated 8-10 membered bicyclic heterocyclyl is optionally substituted by one or more substituents independently selected from the group consisting of halogen, cyano, $C(O)N(R^{10})_2$, $N(R^{10})_2$, =O, and $R^{10}$;

$R^{X2}$ is H, halogen, $C_{1-6}$ alkyl, $C(O)NR^aR^b$, $NR^aR^b$, OH, or $OC_{1-6}$ alkyl;

$R^{X3}$ is H, halogen, $C_{1-6}$ alkyl, $C(O)NR^aR^b$, $NR^aR^b$, OH, or $OC_{1-6}$ alkyl; or $R^{X2}$ and $R^{X3}$, together with the carbon atom to which they are attached, form a 3-6 membered carbocyclyl, wherein the 3-6 membered carbocyclyl is optionally substituted by one or more substituents independently selected from the group consisting of halogen, $C_{1-6}$ alkyl, $C(O)NR^aR^b$, $NR^aR^b$, $OC_{1-6}$ alkyl, and =O;

each $R^{10}$ is independently H, $C_{1-6}$ alkyl, $C_{3-6}$ cycloalkyl, heterocycloalkyl, aryl, or heteroaryl, wherein each $C_{1-6}$ alkyl, $C_{3-6}$ cycloalkyl, heterocycloalkyl, aryl, and heteroaryl is optionally and independently substituted by one or more substituents independently selected from the group consisting of halogen, $C_{1-6}$ alkyl, $C_{1-6}$ haloalkyl, and $C(O)R^{20}$;

each $R^{20}$ is independently halogen, $C_{1-6}$ alkyl, or OH;

$R^Y$ is H, $C_{1-6}$ alkyl, or phenyl;

$R^4$ is H, halogen, cyano, $C_{1-6}$ alkyl, $C(O)NR^aR^b$, or $R^aR^b$, wherein the $C_{1-6}$ alkyl is optionally substituted by one or more substituents independently selected from the group consisting of halogen, $NR^aR^b$, OH, and =O;

$R^5$ is H, halogen, cyano, $C_{1-6}$ alkyl, $C(O)NR^aR^b$, or $R^aR^b$, wherein the $C_{1-6}$ alkyl is optionally substituted by one or more substituents independently selected from the group consisting of halogen, $NR^aR^b$, OH, and =O;

T is —$CH_2$—, —$NR^h$—, —O—, or —$S(O)_w$—;

each $R^h$ is independently H, $C_{1-6}$ alkyl, $C(O)C_{1-6}$ alkyl, $C(O)NR^aR^b$, $C(O)OC_{1-6}$ alkyl, $S(O)_2C_{1-6}$ alkyl, or $S(O)_2NR^aR^b$, wherein each $C_{1-6}$ alkyl, $C(O)C_{1-6}$ alkyl, $C(O)OC_{1-6}$ alkyl, and $S(O)_2C_{1-6}$ alkyl is optionally and independently substituted by one or more substituents independently selected from the group consisting of halogen and OH;

$R^a$ is H or $C_{1-6}$ alkyl, wherein the $C_{1-6}$ alkyl is optionally substituted by one or more substituents independently selected from the group consisting of halogen, cyano, OH, and =O;

$R^b$ is H or $C_{1-6}$ alkyl, wherein the $C_{1-6}$ alkyl is optionally substituted by one or more substituents independently selected from the group consisting of halogen, cyano, OH, and =O;

$R^3$ is H, $C_{1-6}$ alkyl, or phenyl;

m is 0, 1, or 2; and each w is independently 0, 1, or 2.

22. The compound of claim 21, or a pharmaceutically acceptable salt or stereoisomer thereof, wherein A is phenyl, wherein the phenyl is optionally substituted by one, two, or three substituents independently selected from the group consisting of halogen, cyano, and $OR^{10}$.

23. The compound of claim 21, or a pharmaceutically acceptable salt or stereoisomer thereof, wherein A is pyridyl, wherein the pyridyl is optionally substituted by one, two, or three substituents independently selected from the group consisting of halogen, cyano, and $OR^{10}$.

24. The compound of claim 21, or a pharmaceutically acceptable salt or stereoisomer thereof, wherein $R^{X1}$ and A, together with the nitrogen atom to which they are attached, form 1,2,3,4-tetrahydro-1,5-naphthyridinyl.

25. The compound of claim 21, or a pharmaceutically acceptable salt or stereoisomer thereof, wherein $R^Y$ is H or $CH_3$.

26. The compound of claim 21, or a pharmaceutically acceptable salt or stereoisomer thereof, wherein:

$R^4$ is $C_{1-3}$ alkyl or $NR^aR^b$, wherein the $C_{1-3}$ alkyl is optionally substituted by one, two, or three substituents independently selected from the group consisting of halogen, $NR^aR^b$, and OH; and $R^5$ is $C_{1-3}$ alkyl or $NR^aR^b$, wherein the $C_{1-3}$ alkyl is optionally substituted by one, two, or three substituents independently selected from the group consisting of halogen, $NR^aR^b$, and OH.

27. The compound of claim 21, or a pharmaceutically acceptable salt or stereoisomer thereof, wherein:

$R^4$ is $CH_2NH_2$ or $NH_2$; and $R^{5S}$ is $CH_2NH_2$ or $NH_2$.

28. The compound of claim 21, or a pharmaceutically acceptable salt or stereoisomer thereof, wherein T is —$CH_2$— or —O—.

29. The compound of claim 21, or a pharmaceutically acceptable salt or stereoisomer thereof, wherein $R^3$ is H.

30. The compound of claim 21, or a pharmaceutically acceptable salt or stereoisomer thereof, wherein m is 1.

31. The compound of claim 21, or a pharmaceutically acceptable salt or stereoisomer thereof, wherein m is 2.

32. A pharmaceutical composition comprising a pharmaceutically acceptable carrier and a compound of claim 21, or a pharmaceutically acceptable salt or stereoisomer thereof.

33. A method for inhibiting Src homology region 2-containing protein tyrosine phosphatase 2 activity in a subject in need thereof, comprising administering to the subject a therapeutically effective amount of a compound of claim 21, or a pharmaceutically acceptable salt or stereoisomer thereof.

34. The method of claim 33, wherein the subject has a disorder selected from the group consisting of acute myeloid leukemia, breast cancer, colorectal cancer, diabetes, juvenile leukemia, lung cancer, melanoma, myelomonocytic leukemia, neuroblastoma, neutropenia, and Noonan syndrome.

35. The method of claim 33, wherein the method further comprises administering to the subject a therapeutically effective amount of an antibody, an antibody-drug conjugate, an immunomodulator, or a histone deacetylase inhibitor.

36. A compound selected from the group consisting of:

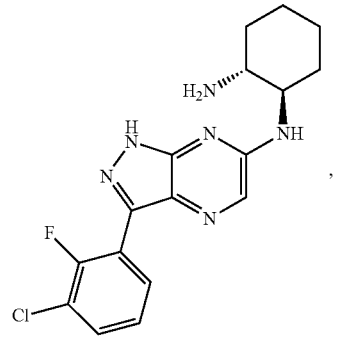

,

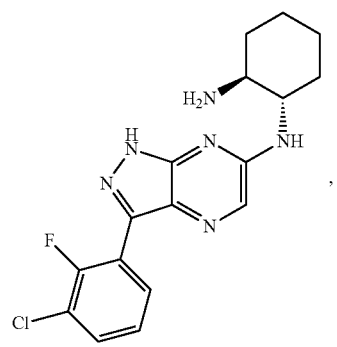

,

79
-continued
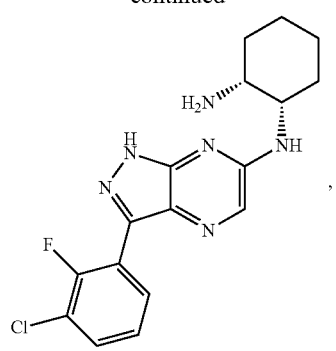
,
80
-continued
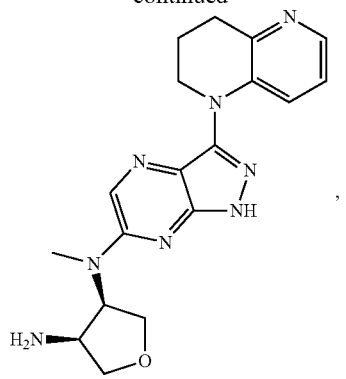
,
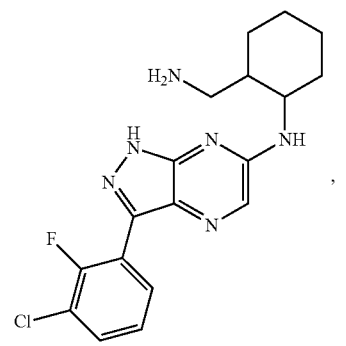
,
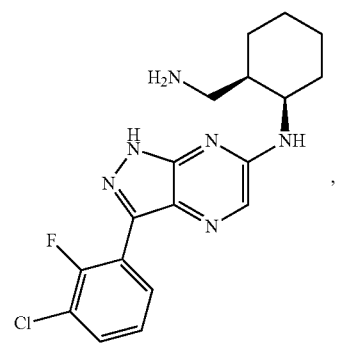
,

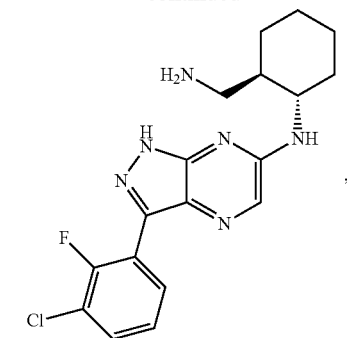
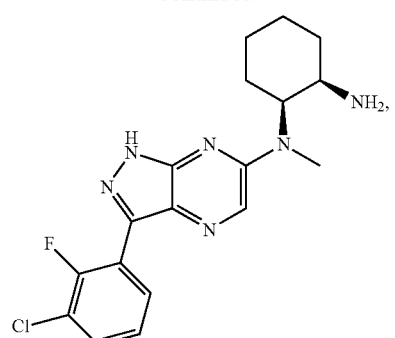
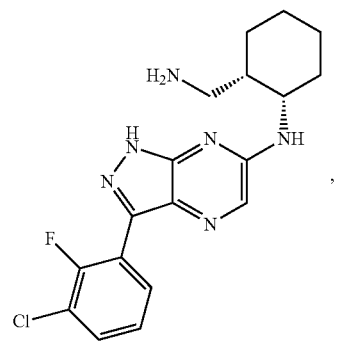
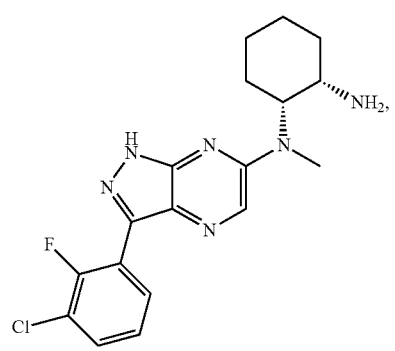
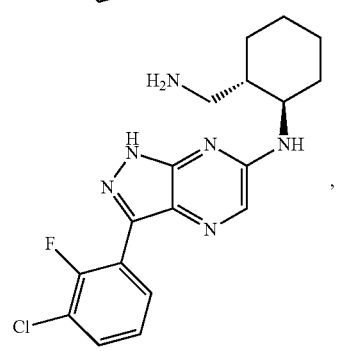
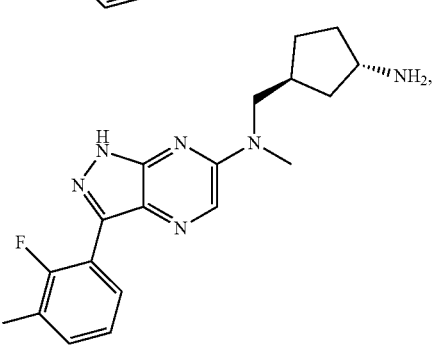
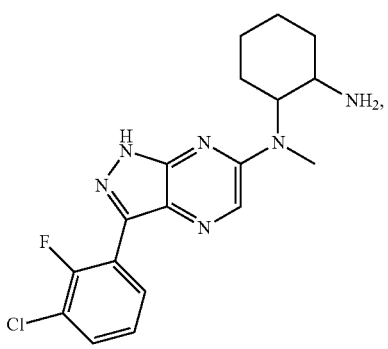
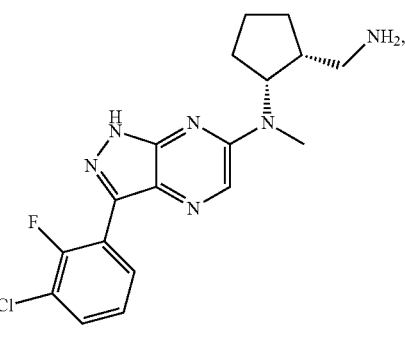
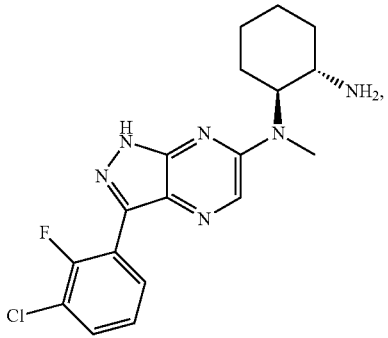
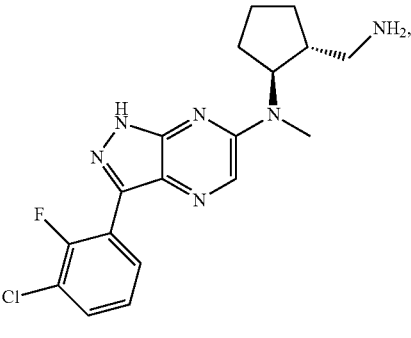

83
-continued
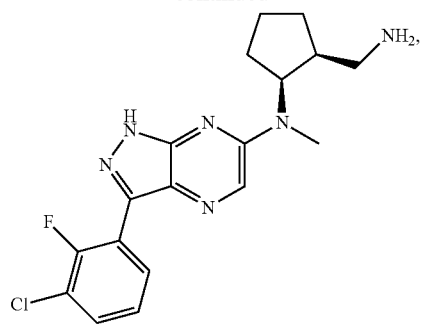
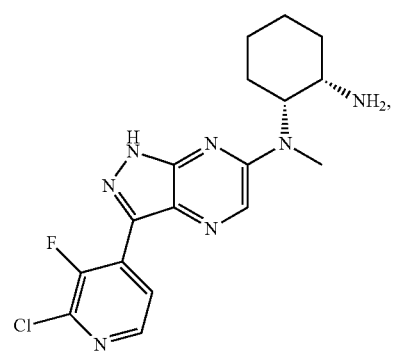
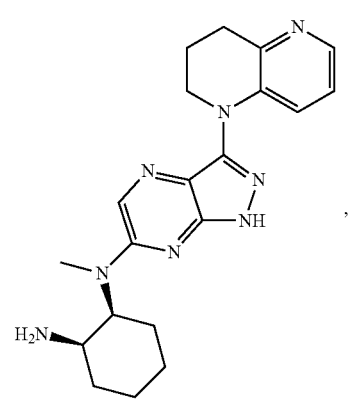
84
-continued
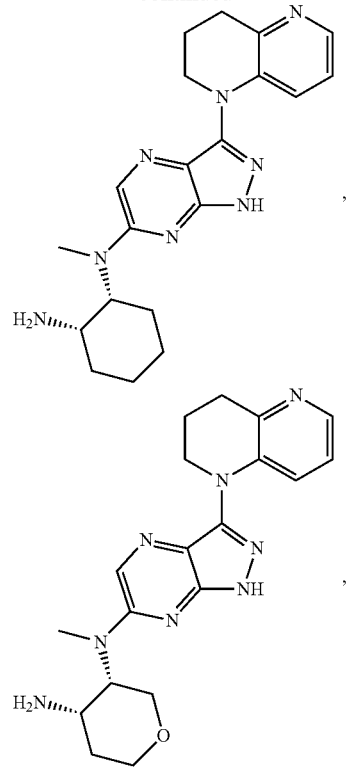
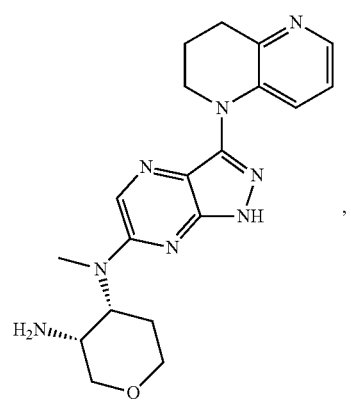
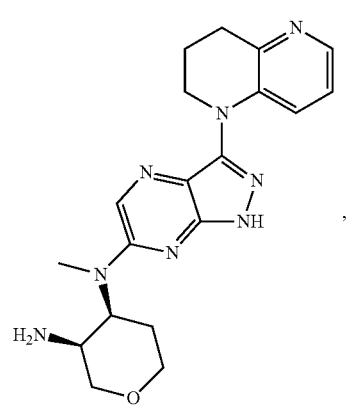

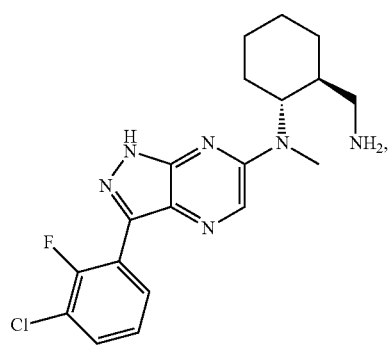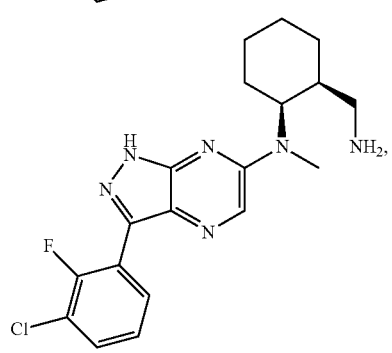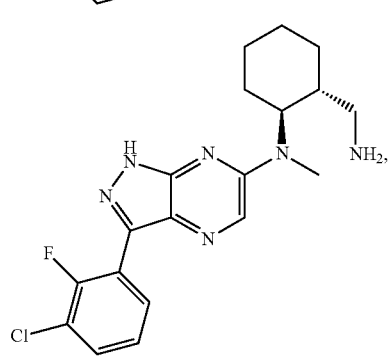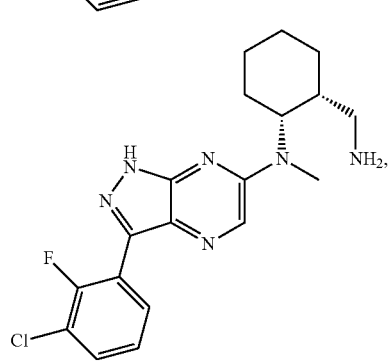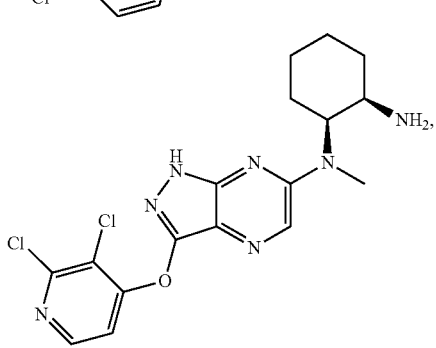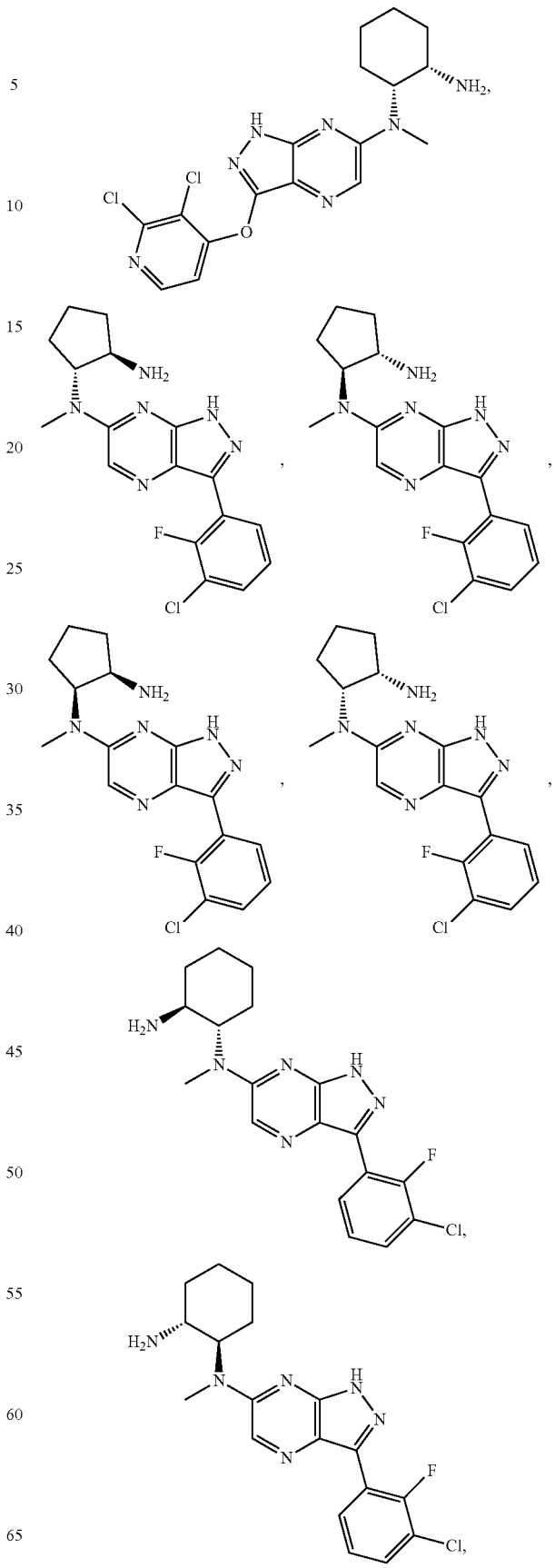

-continued

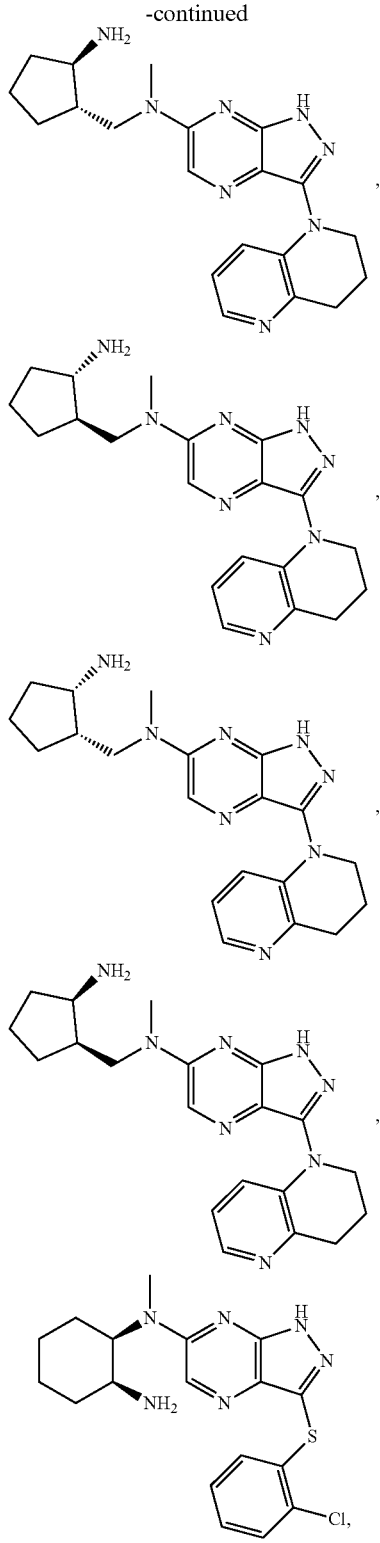

-continued

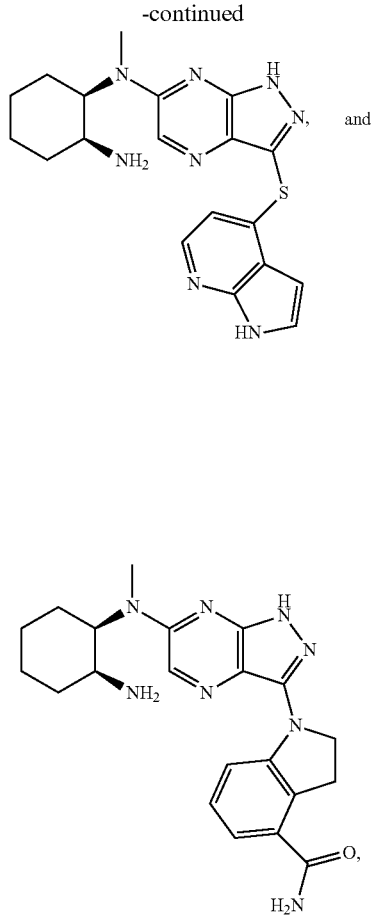

or a pharmaceutically acceptable salt thereof.

37. A pharmaceutical composition comprising a pharmaceutically acceptable carrier and a compound of claim 36, or a pharmaceutically acceptable salt thereof.

38. A method for inhibiting Src homology region 2-containing protein tyrosine phosphatase 2 activity in a subject in need thereof, comprising administering to the subject a therapeutically effective amount of a compound of claim 36, or a pharmaceutically acceptable salt thereof.

39. The method of claim 38, wherein the subject has a disorder selected from the group consisting of acute myeloid leukemia, breast cancer, colorectal cancer, diabetes, juvenile leukemia, lung cancer, melanoma, myelomonocytic leukemia, neuroblastoma, neutropenia, and Noonan syndrome.

40. The method of claim 38, wherein the method further comprises administering to the subject a therapeutically effective amount of an antibody, an antibody-drug conjugate, an immunomodulator, or a histone deacetylase inhibitor.

* * * * *

UNITED STATES PATENT AND TRADEMARK OFFICE
CERTIFICATE OF CORRECTION

| | | |
|---|---|---|
| PATENT NO. | : 11,701,354 B2 | Page 1 of 1 |
| APPLICATION NO. | : 16/651733 | |
| DATED | : July 18, 2023 | |
| INVENTOR(S) | : Taylor et al. | |

It is certified that error appears in the above-identified patent and that said Letters Patent is hereby corrected as shown below:

In the Claims

Column 71,
Line 62, at Claim 1, "P(O)(R$^{10}$)," should read -- P(O)(R$^{10}$)$_2$, --;
Line 64, at Claim 1, "N$^a$R$^b$," should read -- NR$^a$R$^b$, --.

Column 72,
Line 1, at Claim 1, "N$^a$R$^b$," should read -- NR$^a$R$^b$, --;
Line 44, at Claim 1, "N$^a$R$^b$," should read -- NR$^a$R$^b$, --;
Line 54, at Claim 1, "NR$^b$," should read -- NR$^h$, --.

Column 73,
Line 2, at Claim 1, "S(O)C$_{1-6}$ alkyl," should read -- S(O)$_w$C$_{1-6}$ alkyl, --;
Line 26, at Claim 1, "N$^a$R$^b$," should read -- NR$^a$R$^b$, --.

Column 74,
Line 4, at Claim 6, "1,2,3,4-tetrahydro-l,5napthyridinyl" should read
-- 1,2,3,4-tetrahydro-1,5-naphthyridinyl --;
Line 14, at Claim 9, "two, r three" should read -- two, or three --;
Line 16, at Claim 9, "N$^a$R$^b$," should read -- NR$^a$R$^b$, --;
Line 24, at Claim 10, "two, r three" should read -- two, or three --;
Line 26, at Claim 10, "N$^a$R$^b$," should read -- NR$^a$R$^b$, --;
Line 34, at Claim 11, "two, g three" should read -- two, or three --;
Line 36, at Claim 11, "N$^a$R$^b$," should read -- NR$^a$R$^b$, --;
Line 47, at Claim 12, "N$^a$R$^b$," should read -- NR$^a$R$^b$, --.

Column 77,
Line 10, at Claim 21, "R$^a$R$^b$," should read -- NR$^a$R$^b$, --;
Line 14, at Claim 21, "R$^a$R$^b$," should read -- NR$^a$R$^b$, --;
Line 67, at Claim 27, "R$^{5S}$" should read -- R$^5$ --.

Signed and Sealed this
Thirteenth Day of February, 2024

*Katherine Kelly Vidal*
*Director of the United States Patent and Trademark Office*